(12) United States Patent
Motai et al.

(10) Patent No.: US 9,662,167 B2
(45) Date of Patent: May 30, 2017

(54) VAGINAL WALL INCISION INSTRUMENT

(71) Applicant: OLYMPUS CORPORATION, Tokyo (JP)

(72) Inventors: Kosuke Motai, Hidaka (JP); Yusuke Takei, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 14/971,449

(22) Filed: Dec. 16, 2015

(65) Prior Publication Data
US 2016/0095649 A1 Apr. 7, 2016

Related U.S. Application Data

(63) Continuation of application No. PCT/JP2014/080353, filed on Nov. 17, 2014.

(30) Foreign Application Priority Data

Jan. 10, 2014 (JP) .................................. 2014-003132

(51) Int. Cl.
*A61B 18/18* (2006.01)
*A61B 18/14* (2006.01)
(Continued)

(52) U.S. Cl.
CPC .......... *A61B 18/1485* (2013.01); *A61B 17/42* (2013.01); *A61B 2017/4225* (2013.01);
(Continued)

(58) Field of Classification Search
CPC ................ A61B 17/42; A61B 18/1485; A61B 2017/4225; A61B 2018/00077;
(Continued)

(56) References Cited

U.S. PATENT DOCUMENTS 6,032,673 A * 3/2000 Savage .............. A61B 18/1485
128/898
6,077,257 A * 6/2000 Edwards ............ A61B 18/1477
604/101.03

(Continued)

FOREIGN PATENT DOCUMENTS

| JP | H08-500990 A | 2/1996 |
| JP | H10-507384 A | 7/1998 |
| JP | H10-234743 A | 9/1998 |
| JP | H11-336 A | 1/1999 |
| JP | 2010-505457 A | 2/2010 |
| JP | 2010-178766 A | 8/2010 |

(Continued)

OTHER PUBLICATIONS

Jan. 27, 2015 International Search Report issued in International Patent Application No. PCT/JP2014/080353.

*Primary Examiner* — Michael Peffley
*Assistant Examiner* — Amanda Zink
(74) *Attorney, Agent, or Firm* — Oliff PLC

(57) ABSTRACT

A vaginal wall incision instrument includes a main body portion that is capable of being inserted into a vaginal canal; an incision portion that protrudes from a distal portion of the main body portion in a direction intersecting a center line of the vaginal canal and is formed by a conductive material; and an operating portion, wherein the main body portion includes an exterior portion and an interior portion, wherein the interior portion includes a contact portion, wherein a guide hole is configured on the interior portion, wherein the guide hole is capable of guiding the conductive member in a direction toward a boundary between the uterine cervix and the vaginal canal, and wherein the incision portion separates the vaginal canal along a circumference whose center is the center line of rotation by rotating the interior portion about the center line of rotation with respect to the exterior portion.

7 Claims, 18 Drawing Sheets

(51) Int. Cl.
*A61B 17/42* (2006.01)
*A61B 18/00* (2006.01)

(52) U.S. Cl.
CPC ........... *A61B 2018/00077* (2013.01); *A61B 2018/00083* (2013.01); *A61B 2018/00208* (2013.01); *A61B 2018/00279* (2013.01); *A61B 2018/00559* (2013.01); *A61B 2018/00601* (2013.01); *A61B 2018/144* (2013.01); *A61B 2018/1425* (2013.01); *A61B 2018/1475* (2013.01)

(58) Field of Classification Search
CPC  A61B 2018/00083; A61B 2018/00208; A61B 2018/00279; A61B 2018/00559; A61B 2018/00601; A61B 2018/1425; A61B 2018/144; A61B 2018/1475
See application file for complete search history.

(56) References Cited

U.S. PATENT DOCUMENTS

| | | | |
|---|---|---|---|
| 6,156,006 A * | 12/2000 | Brosens | A61B 17/00234 604/104 |
| 2003/0216731 A1 | 11/2003 | Dennis | |
| 2005/0070895 A1 | 3/2005 | Ryan et al. | |
| 2008/0119868 A1* | 5/2008 | Sharp | A61B 17/3421 606/119 |
| 2009/0182329 A1 | 7/2009 | Dycus | |
| 2012/0143209 A1* | 6/2012 | Brecheen | A61B 17/42 606/119 |

FOREIGN PATENT DOCUMENTS

| | | |
|---|---|---|
| WO | 94/00061 A1 | 1/1994 |
| WO | 96/11641 A1 | 4/1996 |
| WO | 2008/005411 A2 | 1/2008 |

* cited by examiner

VAGINAL WALL INCISION INSTRUMENT

This application is a continuation application based on a PCT International Application No. PCT/JP2014/080353, filed on Nov. 17, 2014, whose priority is claimed on Japanese Patent Application No. 2014-003132 filed on Jan. 10, 2014. The content of both the PCT International Application and the Japanese Patent Application are incorporated herein by reference.

BACKGROUND OF THE INVENTION

Field of the Invention

The present invention relates to a vaginal wall incision instrument.

Description of Related Art

In recent years, as a procedure for incising a uterus, a total laparoscopic hysterectomy and a laparoscopic supracervical hysterectomy have been known. The total laparoscopic hysterectomy and the laparoscopic supracervical hysterectomy are procedures in which a laparoscope, a uterine manipulator, and a dissection instrument need to be used. That is, in the total laparoscopic hysterectomy and the laparoscopic supracervical hysterectomy, it is necessary to perform operations of checking an incision target part using the laparoscope, adjusting a separating line using the uterine manipulator, and performing incision using the dissection instrument along the separating line in a coordinated manner.

The laparoscope and the dissection instrument are inserted into an abdominal cavity through an abdominal wall using a trocar. In the total laparoscopic hysterectomy and the laparoscopic supracervical hysterectomy, when the dissection instrument is operated in the abdominal cavity, it is necessary to approach a separating line in a direction intersecting the separating line in a normal state in which the uterus is not tilted. For this reason, straight separation along the separating line is not easy without tilting the uterus using the uterine manipulator. When an operation of tilting the uterus is performed, a cooperative operation of the uterine manipulator, the dissection instrument and the laparoscope is necessary.

As an exemplary instrument for separating biological tissues in a body, a high-frequency incision instrument that can be combined with an endoscope is disclosed in Japanese Unexamined Patent Application, First Publication No. 1998-234743. In Japanese Unexamined Patent Application, First Publication No. 2010-178766, an endoscope for treatment that can be combined with a high-frequency snare configured to cut tissues when a high-frequency current is supplied is disclosed. The endoscope for treatment disclosed in Japanese Unexamined Patent Application, First Publication No. 2010-178766 has an engaging unit that can engage a loop part of the high-frequency snare at a distal end, and can totally resect a body wall using a wire-type part positioned more proximal than the loop part in the high-frequency snare as an incising electrode.

SUMMARY OF THE INVENTION

According to a first aspect of the present invention, a vaginal wall incision instrument includes a main body portion that is capable of being inserted into a vaginal canal; an incision portion that protrudes from a distal portion of the main body portion in a direction intersecting a center line of the vaginal canal and is able to penetrate through the vaginal canal while the main body portion is inserted into the vaginal canal, and is formed by a conductive material; and an operating portion that is disposed at a proximal part of the main body portion and is able to adjust an amount of protrusion of the incision portion, wherein the main body portion includes: an exterior portion that is contactable on an inner wall of the vaginal canal; and an interior portion that is inserted into the exterior portion and rotatable about a predetermined center line of rotation with respect to the exterior portion, and has a distal portion to which the incision portion is fixed, wherein the interior portion includes a contact portion having a surface that is contactable on an uterine cervix, wherein a guide hole configured on the interior portion to guide a distal end portion of the conductive member such that the distal end portion of the conductive member is capable of being advanced and retracted in a direction intersecting the center line of the vaginal canal, wherein the guide hole being capable of guiding the conductive member in a direction toward a boundary between the uterine cervix and the vaginal canal while the contact portion is in contact with the uterine cervix, and wherein the incision portion separates the vaginal canal along a circumference whose center is the center line of rotation by rotating the interior portion about the center line of rotation with respect to the exterior portion, in a state where the incision portion penetrates through the vaginal canal.

According to a second aspect of the present invention, in the vaginal wall incision instrument according to the first aspect, the exterior portion may include an outer tubular member having a tubular shape; and an airtight valve configured to airtightly close a gap between the outer tubular member and the interior portion.

According to a third aspect of the present invention, in the vaginal wall incision instrument according to the first aspect, the exterior portion may include a locking portion that protrudes from an outer circumferential surface of the exterior portion in a radially outward direction of the exterior portion and is lockable to the inner wall of the vaginal canal.

According to a fourth aspect of the present invention, in the vaginal wall incision instrument according to the third aspect, the locking portion may include a plurality of anchors that are lockable to the inner wall of the vaginal canal.

According to a fifth aspect of the present invention, in the vaginal wall incision instrument according to the second aspect, the operating portion may include a shaft body having a substantially bar shape; a serrated portion provided on an external surface of the shaft body; a slider attached to the shaft body; and a convex portion that is provided in the slider and engageable with a plurality of projections constituting the serrated portion.

According to a sixth aspect of the present invention, in the vaginal wall incision instrument according to the second aspect, the interior portion may include a cup-shaped member that is formed in a cup shape whose diameter gradually increases toward a distal side and whose inner surface is a surface that is contactable on the uterine cervix.

According to a seventh aspect of the present invention, in the vaginal wall incision instrument according to the second aspect, the interior portion may include a bar-shaped position-determining member that is formed to be coaxial with the center line of rotation of the interior portion and protrudes toward a distal side.

DETAILED DESCRIPTION OF THE INVENTION (First Embodiment)

Figure 1:
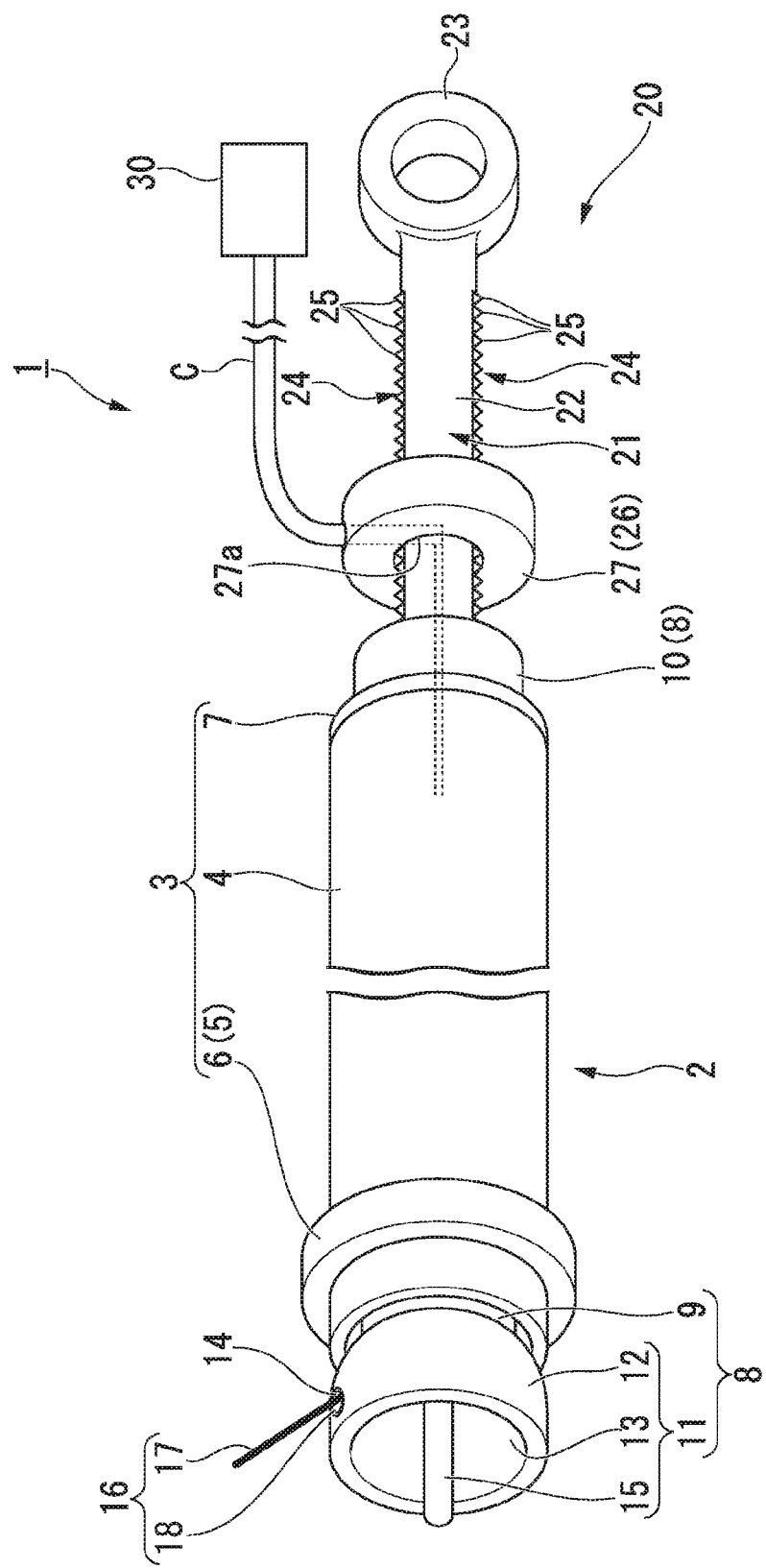
FIG. 1 is a general view of a vaginal wall incision instrument according to a first embodiment of the present invention.
Figure 2:
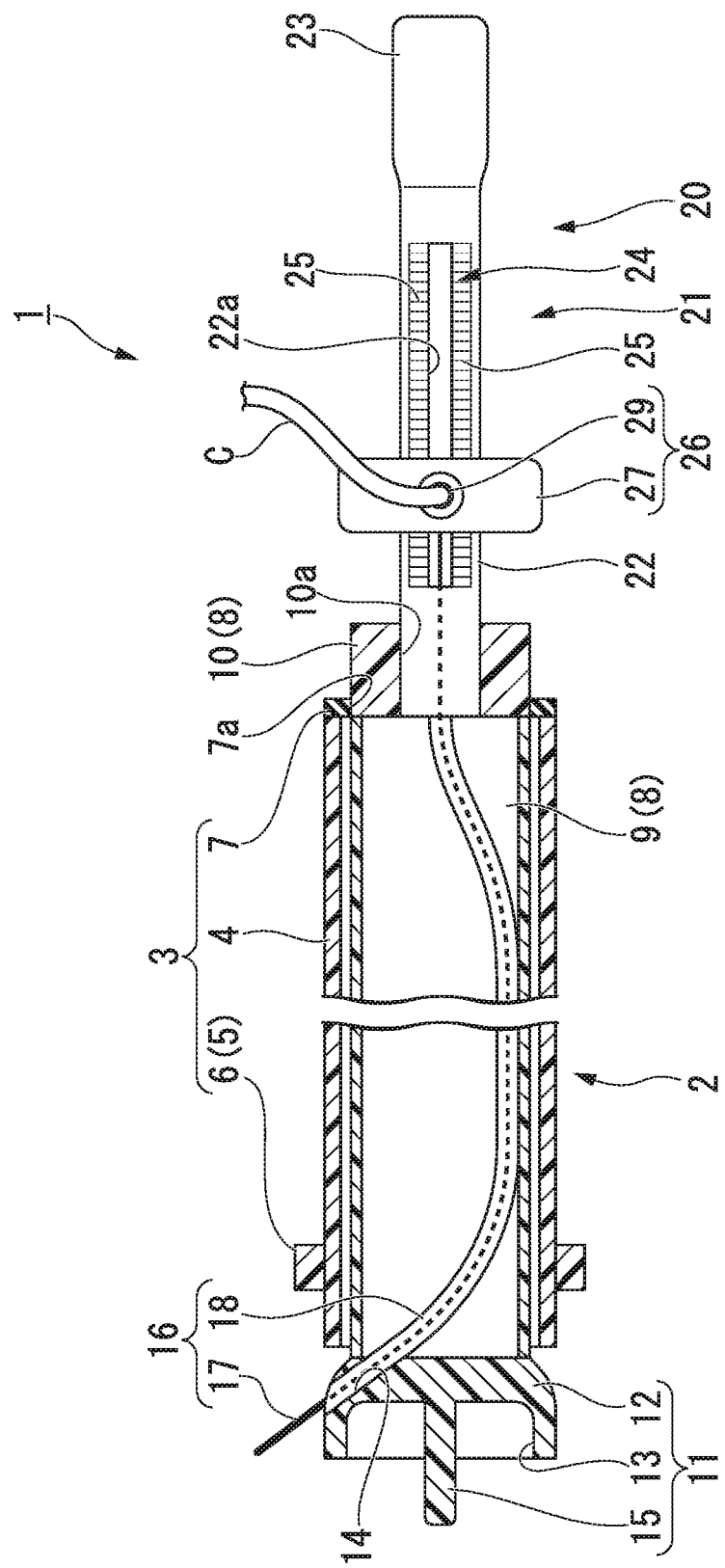
FIG. 2 is a partial cross-sectional view of the vaginal wall incision instrument according to the first embodiment of the present invention.
Figure 3:
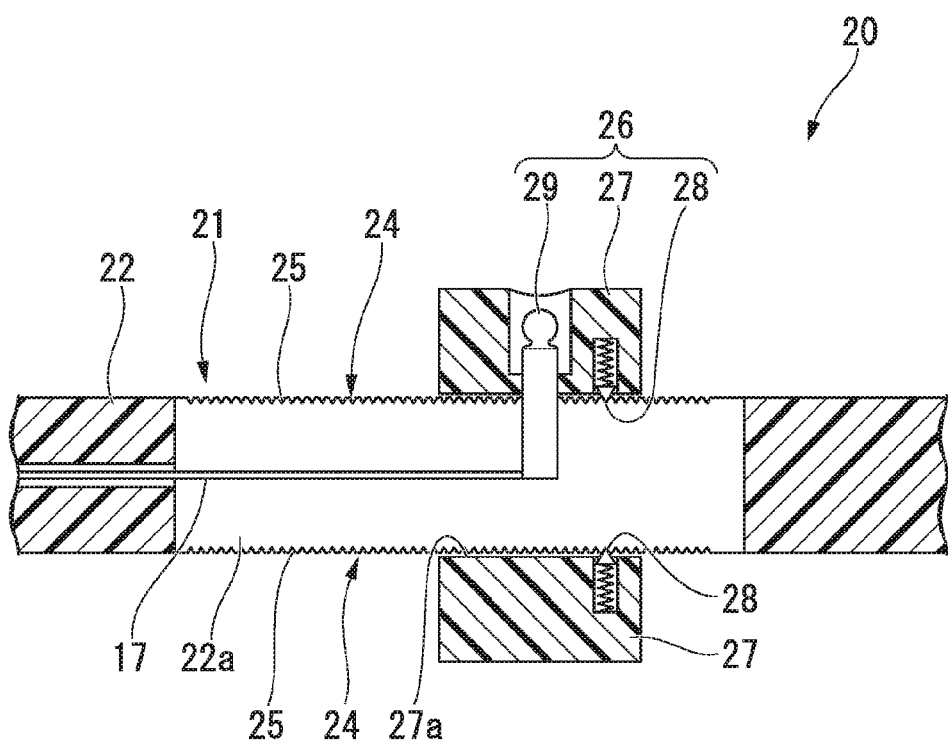
FIG. 3 is a cross-sectional view of an operating portion in the vaginal wall incision instrument according to the first embodiment of the present invention.

A first embodiment of the present invention will be described. FIG. 1 is a general view of a vaginal wall incision instrument 1 according to the present embodiment. FIG. 2 is a partial cross-sectional view of the vaginal wall incision instrument 1 according to the present embodiment. FIG. 3 is a cross-sectional view of an operating portion 20 in the vaginal wall incision instrument 1 according to the present embodiment.

The vaginal wall incision instrument 1 illustrated in FIG. 1 is a medical instrument that can be used to separate a uterus from a vagina in a total laparoscopic hysterectomy and a laparoscopic supracervical hysterectomy.

As illustrated in FIG. 1, the vaginal wall incision instrument 1 has a substantially bar shape as a whole. The vaginal wall incision instrument 1 includes a main body portion 2, an incision portion 16, and the operating portion 20.

As illustrated in FIGS. 1 and 2, the main body portion 2 has a substantially bar shape as a whole. The main body portion 2 can be inserted into a vaginal canal from a distal side. The main body portion 2 includes an exterior portion 3 and an interior portion 8.

The exterior portion 3 forms an outermost layer of the main body portion 2. The exterior portion 3 includes an outer tubular member 4, a locking portion 5, and an airtight valve 7.

The outer tubular member 4 has a tubular shape having an external dimension insertable into the vaginal canal. The outer tubular member 4 is rigid or slightly elastic. In the present embodiment, the outer tubular member 4 is made of a resin or the like. Exemplary materials of the outer tubular member 4 include a fluorine resin (for example, a polytetrafluoroethylene), a nylon resin (for example, nylon), and an olefin resin (for example, a polyethylene and a polypropylene). An outer circumferential surface of the outer tubular member 4 includes a smoothly curved surface that does not damage mucous membranes.

The locking portion 5 includes an annular member 6 fixed to the outer circumferential surface of the outer tubular member 4.

The annular member 6 is arranged in the vicinity of a distal end of the outer tubular member 4. The annular member 6 extends in a circumferential direction of the outer tubular member 4 on the outer circumferential surface of the outer tubular member 4. The annular member 6 and the outer tubular member 4 are fixed by, for example, bonding. The annular member 6 and the outer tubular member 4 may also be integrally formed.

The annular member 6 protrudes in a radially outward direction of the outer tubular member 4 from the outer circumferential surface of the outer tubular member 4. An outer circumferential surface of the annular member 6 has a smoothly curved surface so as not to damage mucous membranes. In the annular member 6, when the vaginal wall incision instrument 1 is used, a gap between the outer tubular member 4 and a vaginal wall is airtightly closed by the annular member 6. When the vaginal wall is incised, the annular member 6 serves to hold the vaginal wall still with respect to the outer tubular member 4.

The airtight valve 7 is a valve for airtightly closing the outer tubular member 4 and the interior portion 8. The airtight valve 7 is fixed to an opening at a proximal end of the outer tubular member 4. The airtight valve 7 has an annular shape including a hole 7a. The interior portion 8 can be inserted into the hole 7a formed in the airtight valve 7. While a connecting member 10 of the interior portion 8 to be described below is inserted into the hole 7a, the airtight valve 7 is slidably in close contact with the connecting member 10 in an airtight state. The airtight valve 7 has elasticity. In addition, a center line of an opening of the hole 7a of the airtight valve 7 corresponds to a center line of the outer tubular member 4. The airtight valve 7 supports the connecting member 10 such that the connecting member 10 is rotatable using the center line of the outer tubular member 4 as a center line of rotation. A material of the airtight valve 7 is not specifically limited as long as the material has elasticity. In the present embodiment, the airtight valve 7 is made of a silicone or urethane material.

The interior portion 8 is rotatable using the center line of the outer tubular member 4 as a center line of rotation inside the outer tubular member 4. As illustrated in FIG. 2, the interior portion 8 includes an inner tubular member 9, the connecting member 10, and a contact portion 11.

The inner tubular member 9 is a tubular member that is arranged inside the outer tubular member 4. An outer diameter of the inner tubular member 9 is slightly smaller than an inner diameter of the outer tubular member 4. A center line of the inner tubular member 9 has substantially the same axis as the center line of the outer tubular member 4. The inner tubular member 9 has a rigidity of a degree at which a power for rotating the operating portion 20 using the center line of the outer tubular member 4 as a center line of rotation can be transmitted to the contact portion 11.

The connecting member 10 connects a distal end of a shaft body 22 of a shaft portion 21 to be described below and a proximal end of the inner tubular member 9 in the operating portion 20. The connecting member 10 has a substantially cylindrical shape including a hole 10a. An outer circumferential surface of the connecting member 10 is in close contact with an inner surface of the hole 7a of the airtight valve 7. The distal end of the shaft body 22 of the operating portion 20 is inserted into the hole 10a formed in the connecting member 10. The connecting member 10 is fixed to the shaft body 22 by, for example, bonding.

The contact portion 11 is disposed at a distal portion of the interior portion 8. When the vaginal wall incision instrument 1 is used, the contact portion 11 is contactable on a vaginal portion of the cervix. The contact portion 11 of the present embodiment includes a cup-shaped member 12 and a position-determining member 15. The cup-shaped member 12 has a cup shape whose diameter gradually increases toward a distal side. The position-determining member 15 protrudes from an inner surface of the cup-shaped member 12.

The cup-shaped member 12 is fixed to a distal end of the inner tubular member 9. The cup-shaped member 12 includes a concave portion 13 and a guide hole 14. The concave portion 13 is contactable on a uterine cervix. The guide hole 14 communicates with an inside of the inner tubular member 9, and is formed to extend in a direction inclined with respect to the center line of the inner tubular member 9.

A distal end of an insulating member 18 having a tubular shape to be described below in the incision portion 16 is fixed to the guide hole 14 of the cup-shaped member 12. The guide hole 14 regulates an advancing and a retracting direction of a conductive member 17 that can protrude from the insulating member 18 of the incision portion 16 in a predetermined direction inclined with respect to the center line of the inner tubular member 9.

The guide hole 14 guides an advancing and a retracting of the conductive member 17 such that, when the conductive member 17 is moved to a distal side of the inner tubular member 9, a distal end of the conductive member 17 obliquely moves in a radially outward direction of the inner tubular member 9. An angle of inclination of a center line of the guide hole 14 with respect to the center line of the inner tubular member 9 is set to an angle at which the distal end of the conductive member 17 is not in contact with the uterine cervix or a uterine corpus but is separated from the uterine cervix or the uterine corpus when the vaginal wall incision instrument 1 is used.

The position-determining member 15 is a bar-shaped member that protrudes toward a distal side from a bottom of the concave portion 13 of the cup-shaped member 12. The position-determining member 15 extends coaxially with the center line of the inner tubular member 9. A protrusion length from the concave portion 13 of the position-determining member 15 has a degree at which at least a distal end of the position-determining member 15 is inserted into an orifice of the uterus while the vaginal portion of the cervix is in contact with the concave portion 13 of the cup-shaped member 12.

Figure 4:
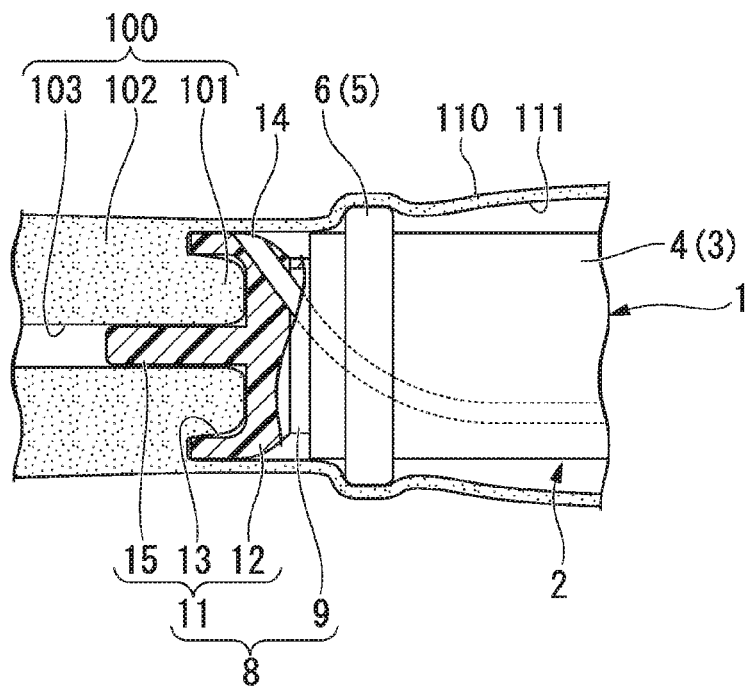
FIG. 4 is a diagram describing an operation of the vaginal wall incision instrument according to the first embodiment of the present invention.

As illustrated in FIG. 4, the position-determining member 15 can connect the orifice of the uterus 103 and the contact portion 11 such that the contact portion 11 is rotatable using an orifice of the uterus 103 as a center line of rotation. While the position-determining member 15 is inserted into the orifice of the uterus 103 and the orifice of the uterus 103 and the contact portion 11 are connected, the conductive member 17 disposed in the guide hole 14 of the cup-shaped member 12 is rotatable using the orifice of the uterus 103 as a center line of rotation.

The incision portion 16 includes the conductive member 17 and the insulating member 18. The conductive member 17 is made of a conductive material. The conductive member 17 is retractably inserted into the insulating member 18 in an advancing and retracting manner.

The conductive member 17 is a conductor such as a metal and has elasticity such that at least a distal portion has a linear shape when no external force is applied. In the present embodiment, the conductive member 17 is formed of an elastic wire having a restoring force that restores the conductive member 17 to a linear shape when no external force is applied.

The distal end of the conductive member 17 is supported by the guide hole 14 formed in the cup-shaped member 12 through the insulating member 18. A proximal end of the conductive member 17 is fixed to a slider 26 of the operating portion 20 to be described below. The proximal end of the conductive member 17 is fixed to a connector 29 (to be described below) provided in the slider 26. The conductive member 17 and the connector 29 are electrically continuous. An intermediate portion of the conductive member 17 is disposed inside the inner tubular member 9.

The insulating member 18 has a cylindrical shape covering the conductive member 17. A distal end of the insulating member 18 is fixed to an inner surface of the guide hole 14 of the cup-shaped member 12. A proximal end of the insulating member 18 is fixed to the distal end of the shaft body 22 of the shaft portion 21 of the operating portion 20.

The operating portion 20 illustrated in FIGS. 2 and 3 is provided at a proximal part of the vaginal wall incision instrument 1. The operating portion 20 is provided to perform an advancing and retracting operation of the conductive member 17 and a rotating operation in which the entire vaginal wall incision instrument 1 is rotated using the center line of the outer tubular member 4 as a center line of rotation. The operating portion 20 includes the shaft portion 21 and the slider 26. The shaft portion 21 extends proximally from a proximal end of the connecting member 10. The slider 26 is attached to the shaft portion 21.

The shaft portion 21 has a substantially bar shape that an operator can grasp. The shaft portion 21 includes the shaft body 22, a ring 23, and a serrated portion 24. The shaft body 22 has a substantially cylindrical shape. The ring 23 is formed at a proximal end of the shaft body 22. The serrated portion 24 is disposed in a row in a longitudinal direction of the shaft body 22 on an external surface of the shaft body 22.

The shaft body 22 has a substantially cylindrical shape into which a proximal part of the conductive member 17 is inserted. In the shaft body 22, a through-hole 22a for connecting the shaft body 22 and the slider 26 is provided to extend in the longitudinal direction of the shaft body 22.

The distal end of the shaft body 22 is inserted into the hole 10a of the connecting member 10. The distal end of the shaft body 22 and the hole 10a of the connecting member 10 are fixed by, for example, bonding. A center line of the shaft body 22 is set to be coaxial with the center line of the inner tubular member 9. Accordingly, when the shaft body 22 is rotated using the center line of the shaft body 22 as a center line of rotation, the inner tubular member 9 and the contact portion 11 fixed to the inner tubular member 9 rotate using the center line of the inner tubular member 9 as a center line of rotation.

The ring 23 has a ring shape whose center line extends in a direction perpendicular to the center line of the shaft body 22 at the proximal end of the shaft body 22. The ring 23 has an inner dimension of a degree at which the operator's finger can pass. An outer diameter of the ring 23 is greater than a diameter of the shaft body 22. When an operation of rotating the shaft body 22 using the center line of the shaft body 22 as a center line of rotation is performed, the operator can hold the ring 23 with his or her finger.

The serrated portion 24 includes a plurality of projections 25 that protrude in a radially outward direction of the shaft body 22 on the external surface of the shaft body 22. The serrated portion 24 is integrally formed with the shaft body 22. In the present embodiment, the plurality of projections 25 constituting the serrated portion 24 are arranged inside the external surface of the shaft body 22 and along an open end of the through-hole 22a formed in the shaft body 22. In the present embodiment, the serrated portions 24 are arranged at two opposite sides with a central axis of the shaft body 22 interposed therebetween and protrude in opposite directions. The plurality of projections 25 constituting the serrated portion 24 are engaged with a convex portion 28 of the slider 26 to be described below. When the convex portion 28 is positioned between a set of adjacent projections 25 in the plurality of projections 25 of the serrated portion 24, it is possible to keep a position of the slider 26 in the serrated portion 24. When the operator applies an external force of a degree at which the convex portion 28 of the slider 26 passes over each of the projections 25 of the serrated portion 24 to the ring 23, the slider 26 is movable with respect to the shaft body 22 in the longitudinal direction of the shaft body 22 at the serrated portion 24.

The slider 26 is a member that can be advanced and retracted in the longitudinal direction of the shaft body 22 with respect to the shaft body 22. The slider 26 is provided to advance and retract the conductive member 17 with respect to the insulating member 18.

The slider 26 includes a cylindrical body 27, the convex portion 28, and the connector 29. The shaft body 22 is inserted into the cylindrical body 27. The convex portion 28 is provided on an inner surface of the cylindrical body 27. The connector 29 is fixed to the cylindrical body 27 and fixed to the proximal end of the conductive member 17.

As illustrated in FIG. 3, in the cylindrical body 27, a through-hole 27a that is slightly larger than an outer diameter of the shaft body 22 is formed. An inner diameter of the cylindrical body 27 is smaller than an outer diameter of the ring 23 illustrated in FIG. 2. The operator manually advances and retracts the cylindrical body 27 with respect to the shaft body 22. An external surface of the cylindrical body 27 may have a configuration into which the operator can insert his or her finger.

The convex portion 28 protrudes from an inner surface of the through-hole 27a formed in the slider 26 toward an inside of the cylindrical body 27. The convex portion 28 is pressed against the serrated portion 24 by a resilient unit, for example, a spring.

As illustrated in FIGS. 2 and 3, the connector 29 is provided to attach a cord C to be connected to a high-frequency power supply device 30. The connector 29 is fixed to a hole connecting the external surface of the cylindrical body 27 and the inner surface of the through-hole 27a of the cylindrical body 27 and protrudes inward through the through-hole 27a of the cylindrical body 27. A part protruding inward through the through-hole 27a of the cylindrical body 27 of the slider 26 in the connector 29 extends to a center line part of the shaft body 22 through the through-hole 22a of the shaft body 22 and is fixed to the proximal end of the conductive member 17. Accordingly, when the slider 26 is advanced and retracted with respect to the shaft body 22 in the longitudinal direction of the shaft body 22, the slider 26 and the connector 29 are integrally advanced and retracted so that the conductive member 17 is advanced and retracted with respect to the shaft body 22 in the longitudinal direction of the shaft body 22.

Next, an operation of the vaginal wall incision instrument 1 according to the present embodiment will be described.

Specifically, a total laparoscopic hysterectomy (TLH) using the vaginal wall incision instrument 1 according to the present embodiment will be exemplified.

In the total laparoscopic hysterectomy, treatment is performed on a plurality of ligaments, blood vessels, adhesive tissues, and adnexa supporting a uterus and then the uterus is extracted according to treatment of incising the vaginal canal.

In the present embodiment, the uterus is separated from a vaginal canal using a boundary part between an inguinal region and the vaginal canal of the uterus as a separating line. First, according to a known procedure, treatment is performed on the plurality of ligaments, blood vessels, adhesive tissues, and adnexa supporting the uterus. Such a procedure is performed under a laparoscope. In addition, as necessary, a uterine manipulator may be inserted into the uterus from the vaginal canal to adjust a position of the uterus.

The vaginal wall incision instrument 1 according to the present embodiment is prepared in a state (refer to FIG. 1) in which the high-frequency power supply device 30 is connected to the connector 29. The slider 26 of the operating portion 20 is positioned at a proximal part in the shaft portion 21. The distal end of the conductive member 17 is positioned more proximal than the distal end of the insulating member 18. When the vaginal wall incision instrument 1 is used, first, the operator inserts the vaginal wall incision instrument 1 according to the present embodiment into a vaginal canal 110. As illustrated in FIG. 4, the vaginal wall incision instrument 1 is inserted into the vaginal canal 110 from the contact portion 11 until the contact portion 11 is in contact with a part 101 (refer to FIG. 4, hereinafter referred to as a "first part 101") facing an inside of the vaginal canal 110 of a uterine cervix 102.

As illustrated in FIG. 4, in the contact portion 11, the concave portion 13 of the cup-shaped member 12 is in contact with the uterine cervix 102 to cover the first part 101. The guide hole 14 formed in the cup-shaped member 12 supports the conductive member 17 through the insulating member 18 such that, in a direction substantially along an external surface of the uterine cervix 102, the conductive member 17 can protrude in a direction inclined with respect to the center line of the inner tubular member 9. In this case, a protrusion direction of a distal portion of the conductive member 17 is a linear direction intersecting a boundary part between the uterine cervix 102 and the vaginal canal 110. The distal end of the position-determining member 15 is inserted into the orifice of the uterus 103.

Figure 5:
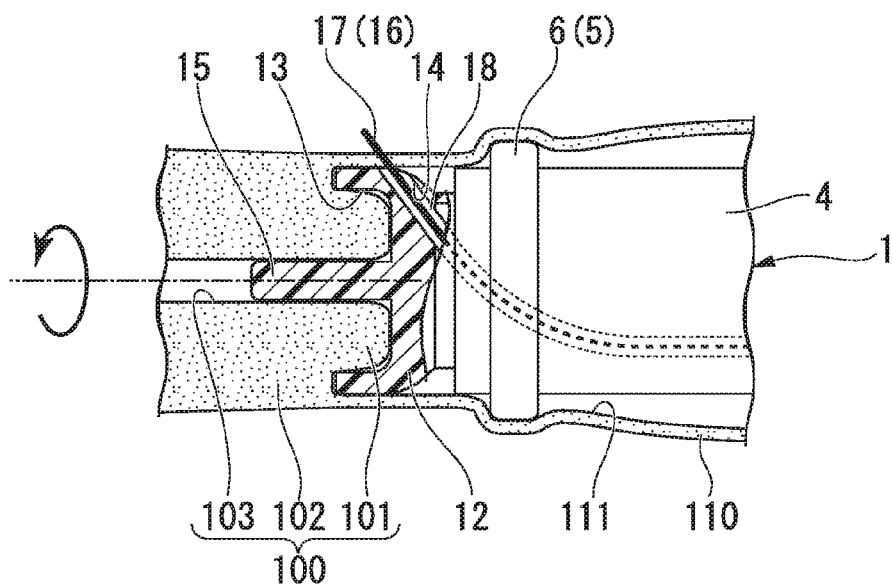
FIG. 5 is a diagram describing an operation of the vaginal wall incision instrument according to the first embodiment of the present invention.

The operator checks that other tissues do not come in contact with the vicinity of the boundary part between the uterine cervix 102 and the vaginal canal 110 under a laparoscope. Then, the slider 26 (refer to FIG. 3) is moved toward a distal side of the shaft body 22. As a result, as illustrated in FIG. 5, the conductive member 17 protrudes toward the boundary part between the uterine cervix 102 and the vaginal canal 110. As necessary, the operator may move the slider 26 toward the distal side of the shaft body 22 while a high-frequency current is supplied to the conductive member 17 using the high-frequency power supply device 30. The distal end of the conductive member 17 penetrates through a vaginal wall 111 in the boundary part between the uterine cervix 102 and the vaginal canal 110 and penetrates through the vaginal wall 111 to reach an inside of the abdominal cavity. A position of the distal end of the conductive member 17 can be recognized using the laparoscope. The operator stops an operation of the slider 26 at a position at which the conductive member 17 penetrates through the vaginal wall 111. Since the convex portion 28 of the slider 26 and the projections 25 of the serrated portion 24 of the shaft body 22 are engaged, the slider 26 is held at a position at which the operator stopped the operation of the slider 26. Accordingly, even when the operator releases his or her finger from the slider 26, the conductive member 17 remains penetrated through the vaginal wall 111.

After the conductive member 17 penetrates through the vaginal wall 111, the operator rotates the shaft body 22 of the operating portion 20 using the center line of the shaft body 22 as a center line of rotation while a high-frequency current is supplied to the conductive member 17. The shaft body 22 may be rotated in any direction. As a result, the shaft body 22 rotates the cup-shaped member 12 through the connecting member 10 and the inner tubular member 9. The cup-shaped member 12 rotates using the orifice of the uterus 103 as a center line of rotation when the distal end of the position-determining member 15 is inserted into the orifice of the uterus 103. The outer tubular member 4 does not rotate by a rotating operation of the shaft body 22. For this reason, while the locking portion 5 provided in the outer tubular member 4 is locked on an inner surface of the vaginal wall 111, the conductive member 17 incises the vaginal wall 111 while rotating in a circumferential direction of the vaginal wall 111.

Figure 6:
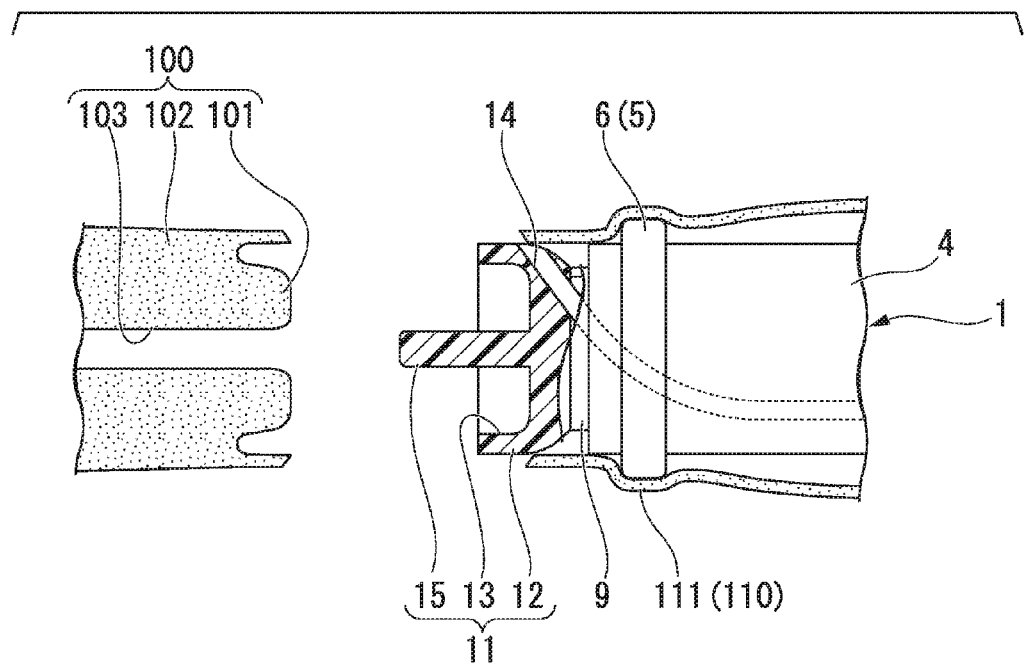
FIG. 6 is a diagram describing an operation of the vaginal wall incision instrument according to the first embodiment of the present invention.

When the conductive member 17 rotates in the circumferential direction of the vaginal wall 111 one full time, the conductive member 17 returns to a penetration part of the vaginal wall 111. That is, as illustrated in FIG. 6, the vaginal wall 111 is separated over the entire circumference using the boundary part between the uterine cervix 102 and the vaginal canal 110 as the separating line. Accordingly, a uterus 100 is separated from the vaginal canal 110.

When the uterus 100 is separated from the vaginal canal 110, the uterus 100 is extracted to the outside of the body through the vaginal canal 110 or through an incised part formed in an abdominal wall according to a known procedure.

In the vaginal wall incision instrument 1 according to the present embodiment, when the shaft body 22 of the operating portion 20 is rotated using the center line of the shaft body 22 as a center line of rotation, the conductive member 17 that has penetrated through the vaginal canal 110 can be rotated with the center line of the outer tubular member 4 and the inner tubular member 9 as a center line of rotation. An external surface of the outer tubular member 4 is in contact with an inner surface of the vaginal canal 110, and the vaginal canal 110 has a tubular shape whose center is aligned with the center line of the outer tubular member 4. Therefore, when the conductive member 17 rotates with the center line of the outer tubular member 4 and the inner tubular member 9 as a center line of rotation, the conductive member 17 can separate the vaginal canal 110 along a circular separating line that extends in a circumferential direction of the vaginal canal 110 in a plane perpendicular to a center line of the vaginal canal 110, in the vaginal canal 110 having a tubular shape.

That is, the vaginal wall incision instrument 1 according to the present embodiment can separate the vaginal canal 110 along an ideal separating line in the boundary part between the uterine cervix 102 and the vaginal canal 110. In addition, as an operation of separating the vaginal canal 110, only an operation in which the shaft body 22 is rotated using the center line of the shaft body 22 as a center line of rotation is performed while a high-frequency current is supplied to the conductive member 17, and a cooperative operation of a plurality of instruments is unnecessary. That is, when the vaginal canal 110 is held by the outer tubular member 4, position determining for matching a position of the conductive member 17 with a separating line has already been performed. Therefore, the operator can separate the vaginal wall 111 along an ideal separating line when only the rotating operation of the shaft body 22 is performed.

In the vaginal wall incision instrument 1 according to the present embodiment, the conductive member 17 rotates such that separation starts from a part in which the conductive member 17 penetrates through the vaginal wall 111, and when the separation ends, the conductive member 17 is returned to the penetration part. Therefore, a position of the conductive member 17 is easily adjusted during the separating operation and workability is excellent.

In the vaginal wall incision instrument 1 according to the present embodiment, the distal end portion of the conductive member 17 advances and retracts in a direction intersecting the center line of the vaginal canal 110, and the conductive member 17 penetrates through the vaginal wall 111 in a radially outward direction of the vaginal canal 110 as it advances to the distal side. Therefore, compared to when the conductive member 17 protrudes in a direction perpendicular to the center line of the vaginal canal 110, a separating operation using the vaginal wall incision instrument 1 according to the present embodiment can preserve the vaginal canal 110 with a small ablation amount of the vaginal canal 110.

Further, when the operator causes the conductive member 17 to penetrate through the vaginal canal 110 or when the operator separates the vaginal canal 110 over the entire circumference using the conductive member 17, the conductive member 17 is less likely to be in contact with the uterine cervix 102. In addition, compared to when the conductive member 17 protrudes in a direction perpendicular to the center line of the vaginal canal 110, it is possible to decrease a possibility of erroneous contact of the distal end of the conductive member 17 with other biological tissues inside the abdominal cavity.

In addition, while the concave portion 13 of the cup-shaped member 12 is in contact with the first part 101, the cup-shaped member 12 is stable while covering the first part 101. Therefore, when the operator only moves the slider 26 to the distal side while the concave portion 13 of the cup-shaped member 12 is pressed against the first part 101, the conductive member 17 can easily penetrate through the boundary part between the uterine cervix 102 and the vaginal canal 110.

While the concave portion 13 of the cup-shaped member 12 is in contact with the first part 101, the cup-shaped member 12 is rotatable using the first part 101 as a center line of rotation. Therefore, when the operator only rotates the shaft body 22 while the concave portion 13 of the cup-shaped member 12 is pressed against the first part 101, the conductive member 17 can be easily rotated along a separating line of the boundary part between the uterine cervix 102 and the vaginal canal 110.

Since the guide hole 14 supporting the conductive member 17 through the insulating member 18 is formed in the cup-shaped member 12, the distal end of the conductive member 17 is easily accessible at the boundary part between the uterine cervix 102 and the vaginal canal 110.

In the vaginal wall incision instrument 1 according to the present embodiment, the cup-shaped member 12 is rotatable using the orifice of the uterus 103 as a center line of rotation by the position-determining member 15. The position-determining member 15 suppresses a positional deviation of the uterus 100 with respect to the vaginal canal 110 and a positional deviation of the vaginal wall incision instrument 1 with respect to the uterus 100. Therefore, it is possible to suppress a positional deviation from a separating line of the conductive member 17 during a separating procedure of the vaginal wall 111 using the conductive member 17.

The locking portion 5 provided on the outer circumferential surface of the outer tubular member 4 holds the vaginal wall 111 such that positions of the outer tubular member 4 and the vaginal wall 111 are not deviated. Therefore, the vaginal canal 110 is less likely to be twisted during the separating operation, and the vaginal wall 111 is easily separated along an ideal separating line.

The airtight valve 7 for maintaining the outer tubular member 4 and the interior portion 8 in an airtight state is provided at the exterior portion 3. Therefore, when a gas is input to the abdominal cavity in order to easily perform a procedure under a laparoscope, an amount of gas leaked from a gap between the outer tubular member 4 and the interior portion 8 is minimized, and the outer tubular member 4 and the interior portion 8 are rotatable using the center line of the outer tubular member 4 as a center line of rotation.

The locking portion 5 provided in the outer tubular member 4 can also suppress a gas filled in the abdominal cavity according to gas supply from leaking.

(Modification)

Figure 7:
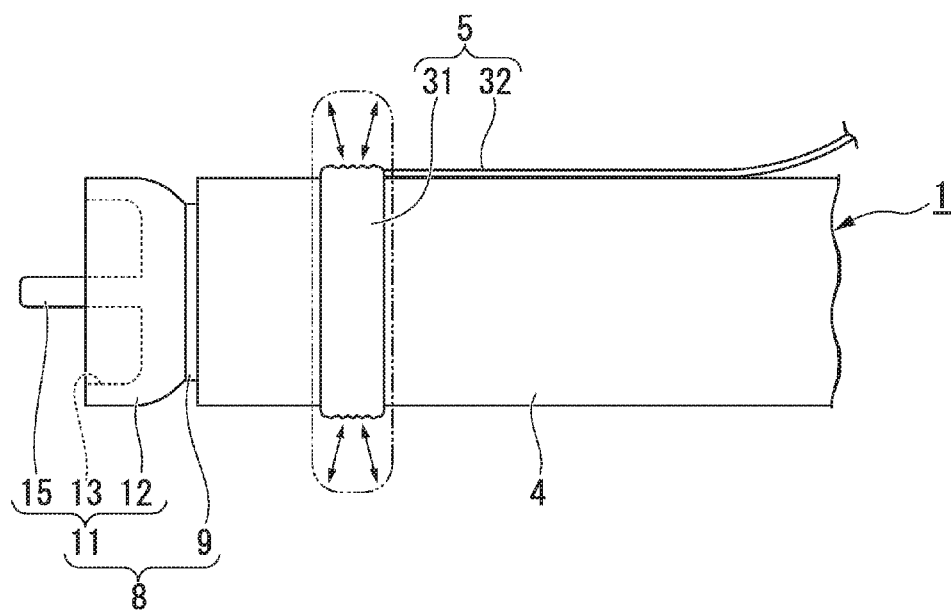
FIG. 7 is a side view of a configuration of a modification of the vaginal wall incision instrument according to the first embodiment of the present invention.

Next, a modification of the present embodiment will be described. FIG. 7 is a side view of a configuration of a modification of the vaginal wall incision instrument according to the embodiment.

The present modification has a different configuration from the embodiment in that the locking portion 5 described in the embodiment includes a balloon 31 and an air feed conduit 32 instead of the annular member 6, as illustrated in FIG. 7.

The balloon 31 has an annular shape whose center is aligned with the center line of the outer tubular member 4 on the outer circumferential surface of the outer tubular member 4 and is fixed to the outer circumferential surface of the outer tubular member 4. The balloon 31 has an expandable membrane that inflates when a liquid or a gas is filled therein. When a liquid or a gas is filled inside the balloon 31, the balloon 31 is inflated in a donut shape.

The air feed conduit 32 is a tubular member whose distal end communicates with an inside of the balloon 31 and whose proximal end is connected to a pump. The air feed conduit 32 is fixed to, for example, the external surface of the outer tubular member 4.

In addition, the air feed conduit 32 may be drawn into the outer tubular member 4 through the outer tubular member 4 and extend to a proximal side of the main body portion 2 through a gap between the outer tubular member 4 and the interior portion 8.

In the present modification, when an inflation diameter of the balloon 31 is adjusted, it is possible to adjust a pressing force of the balloon 31 against the vaginal wall 111. Accordingly, in the present modification, it is possible to lock the outer tubular member 4 to the vaginal wall 111 with an appropriate locking force corresponding to individual differences of patients.

(Second Embodiment)

Next, a second embodiment of the present invention will be described. In embodiments to be described below, components having the same functions or structures as those in the vaginal wall incision instrument 1 according to the above-described first embodiment are denoted by the same reference numerals as in the first embodiment, and redundant descriptions thereof will be omitted.

Figure 8:
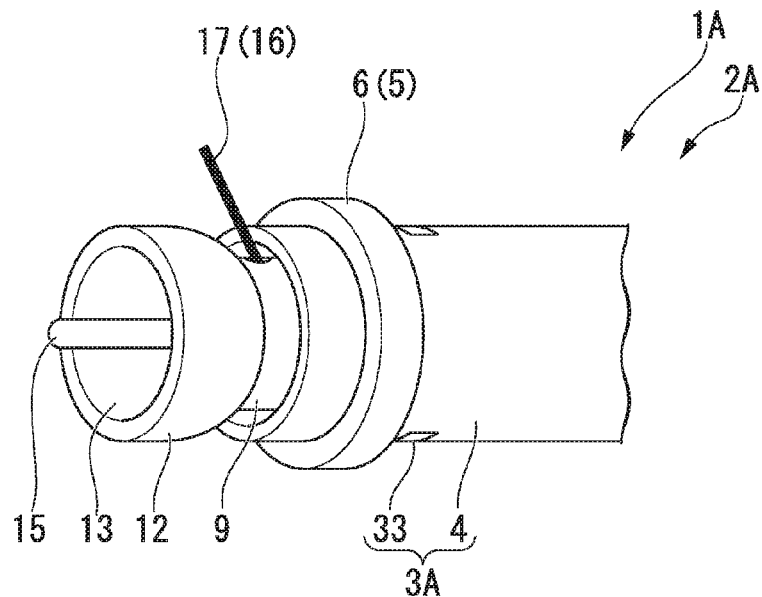
FIG. 8 is a perspective view of a part of a vaginal wall incision instrument according to a second embodiment of the present invention.
Figure 9:
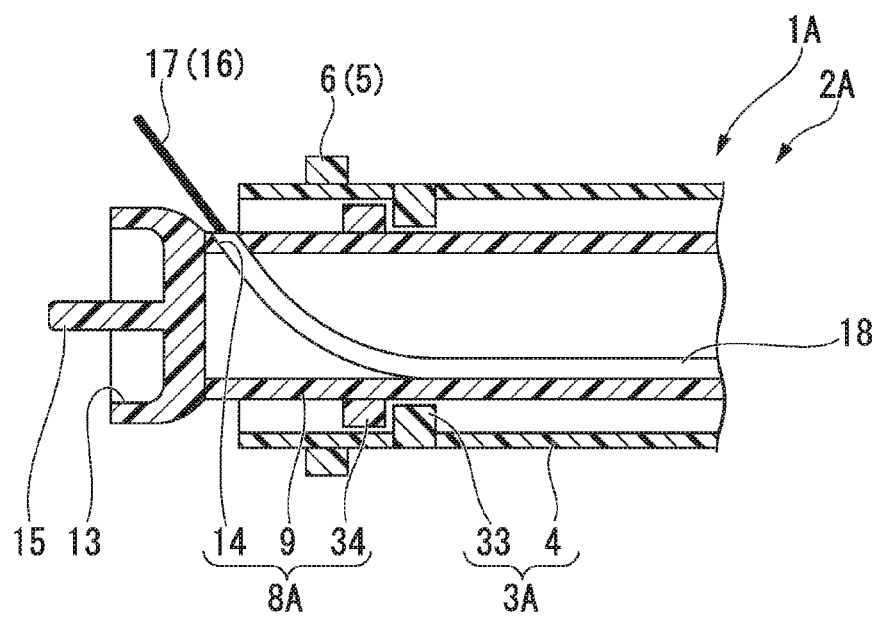
FIG. 9 is a cross-sectional view of a distal portion of the vaginal wall incision instrument according to the second embodiment of the present invention.

FIG. 8 is a perspective view of a part of a vaginal wall incision instrument 1A according to the present embodiment. FIG. 9 is a cross-sectional view of a distal portion of the vaginal wall incision instrument 1A according to the present embodiment.

As illustrated in FIGS. 8 and 9, the vaginal wall incision instrument 1A according to the present embodiment includes a main body portion 2A whose configuration is different from the main body portion 2 described in the first embodiment.

As illustrated in FIG. 9, the main body portion 2A includes an exterior portion 3A and an interior portion 8A. The exterior portion 3A has a different configuration from the exterior portion 3 of the first embodiment in that a first stopper 33 is provided on an inner circumferential surface of the outer tubular member 4. The interior portion 8A has a different configuration from the interior portion 8 of the first embodiment in that a second stopper 34 is provided on an outer circumferential surface of the inner tubular member 9 and the guide hole 14 is provided in the inner tubular member 9 instead of the cup-shaped member 12. The present embodiment includes the same incision portion 16 and operating portion 20 as those in the first embodiment.

The first stopper 33 provided at the outer tubular member 4 extends in the circumferential direction of the outer tubular member 4 and is provided over an entire circumference of the outer tubular member 4 on the inner circumferential surface of the outer tubular member 4. The first stopper 33 protrudes from the inner circumferential surface of the outer tubular member 4 radially inward toward the outer tubular member 4.

The second stopper 34 provided at the inner tubular member 9 extends in a circumferential direction of the inner tubular member 9 and is provided over an entire circumference of the inner tubular member 9 on the outer circumferential surface of the inner tubular member 9. The second stopper 34 protrudes from the outer circumferential surface of the inner tubular member 9 in a radially outward direction of the inner tubular member 9. There is a clearance between an outer circumferential surface of the second stopper 34 and the outer tubular member 4. The clearance has a size of a degree at which the second stopper 34 is rotatable using the center line of the outer tubular member 4 as a center line of rotation with respect to the outer tubular member 4. The second stopper 34 is positioned more distal than the first stopper 33. An external surface of a proximal side in the second stopper 34 is contactable on an external surface of a distal side in the first stopper 33.

Similarly to the first embodiment, the guide hole 14 formed in the inner tubular member 9 guides the conductive member 17 in a direction inclined with respect to the center line of the inner tubular member 9. In addition, while the second stopper 34 is in contact with the first stopper 33, a gap of a degree at which the conductive member 17 can protrude is open between the distal end of the outer tubular member 4 and the interior portion 8A. Accordingly, in the present embodiment, the conductive member 17 protrudes from a gap between the distal end of the outer tubular member 4 and the interior portion 8A.

Similarly to the first embodiment, the vaginal wall incision instrument 1A according to the present embodiment can also separate the vaginal canal 110 along an ideal separating line set in a boundary between the uterine cervix 102 and the vaginal canal 110.

(Third Embodiment)

Figure 10:
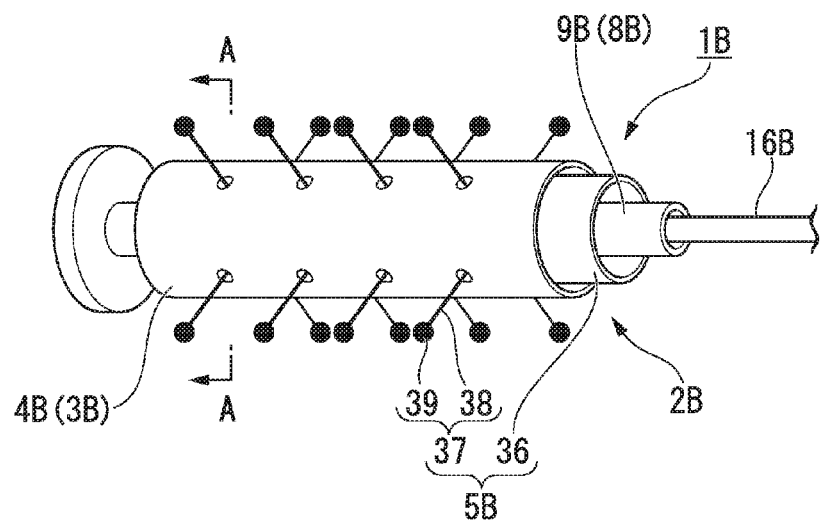
FIG. 10 is a perspective view of a main body portion of a vaginal wall incision instrument according to a third embodiment of the present invention.
Figure 11:
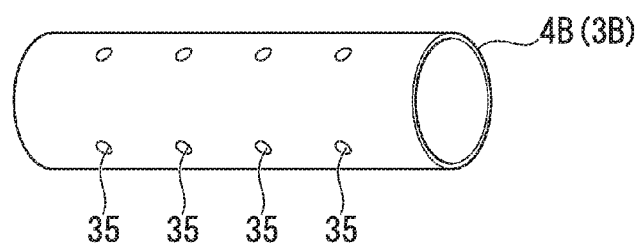
FIG. 11 is a perspective view of an outer tubular member of the vaginal wall incision instrument according to the third embodiment of the present invention.
Figure 12:
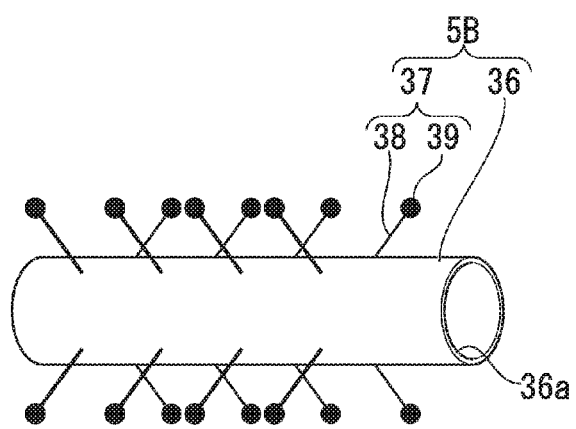
FIG. 12 is a perspective view of an intermediate tubular member of the vaginal wall incision instrument according to the third embodiment of the present invention.
Figure 13:
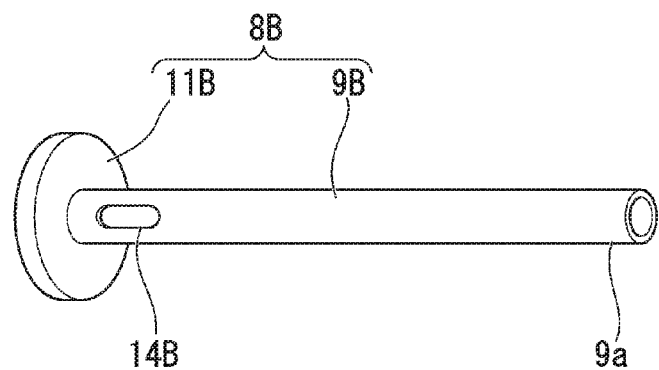
FIG. 13 is a perspective view of an inner tubular member of the vaginal wall incision instrument according to the third embodiment of the present invention.
Figure 14:
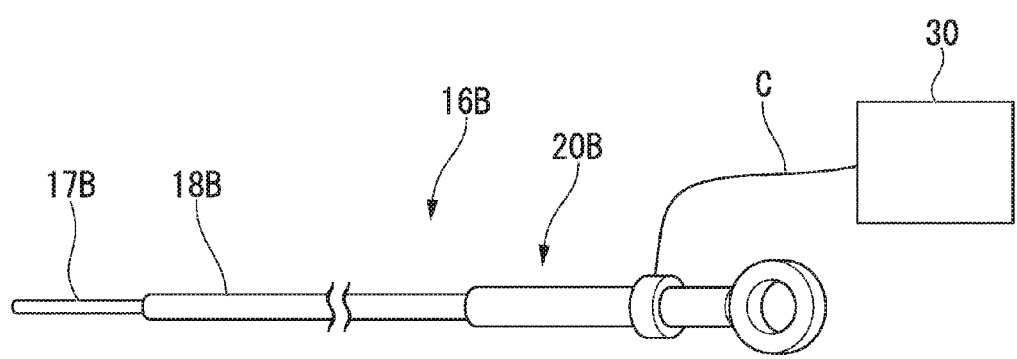
FIG. 14 is a perspective view of an incision portion of the vaginal wall incision instrument according to the third embodiment of the present invention.
Figure 15:
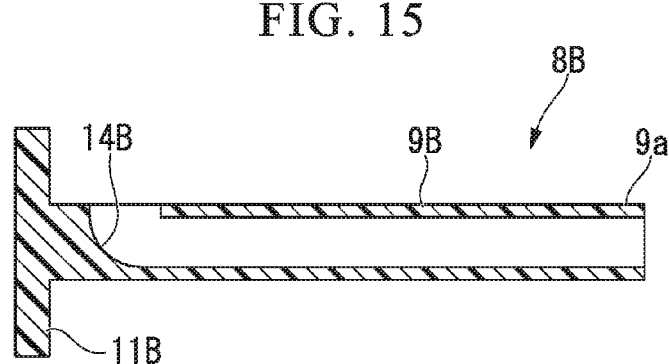
FIG. 15 is a cross-sectional view of the inner tubular member of the vaginal wall incision instrument according to the third embodiment of the present invention.
Figure 16:
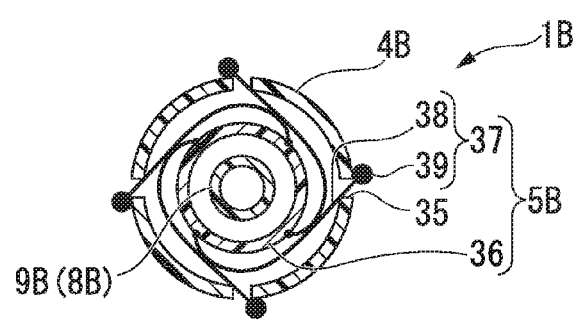
FIG. 16 is a diagram describing an operation of the vaginal wall incision instrument according to the third embodiment of the present invention and is a cross-sectional view taken along line A-A of FIG. 10.
Figure 17:
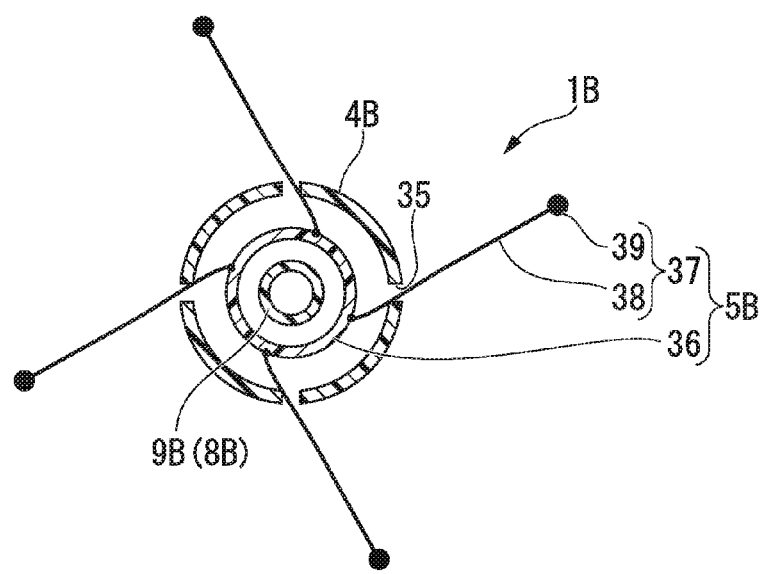
FIG. 17 is a diagram describing an operation of the vaginal wall incision instrument according to the third embodiment of the present invention and is a cross-sectional view taken along line A-A of FIG. 10.

Next, a third embodiment of the present invention will be described. FIG. 10 is a perspective view of a main body portion of a vaginal wall incision instrument 1B according to the present embodiment. FIG. 11 is a perspective view of an outer tubular member 4B of the vaginal wall incision instrument 1B according to the present embodiment. FIG. 12 is a perspective view of an intermediate tubular member 36 of the vaginal wall incision instrument 1B according to the present embodiment. FIG. 13 is a perspective view of an inner tubular member 9B of the vaginal wall incision instrument 1B according to the present embodiment. FIG. 14 is a perspective view of an incision portion 16B of the vaginal wall incision instrument 1B according to the present embodiment. FIG. 15 is a cross-sectional view of the inner tubular member 9B of the vaginal wall incision instrument 1B according to the present embodiment. FIG. 16 is a diagram describing an operation of the vaginal wall incision instrument 1B according to the present embodiment and is a cross-sectional view taken along line A-A of FIG. 10. FIG. 17 is a diagram describing an operation of the vaginal wall incision instrument 1B according to the present embodiment and is a cross-sectional view taken along line A-A of FIG. 10.

As illustrated in FIG. 10, the vaginal wall incision instrument 1B according to the present embodiment includes a main body portion 2B whose configuration is different from the main body portion 2 described in the first embodiment. The vaginal wall incision instrument 1B according to the present embodiment includes the incision portion 16B instead of the incision portion 16 described in the third embodiment.

The main body portion 2B includes an exterior portion 3B, a locking portion 5B, and an interior portion 8B. The exterior portion 3B includes the outer tubular member 4B whose shape is different from the outer tubular member 4 described in the first embodiment. The locking portion 5B is disposed inside the exterior portion 3B and has a different configuration from the locking portion 5 described in the first embodiment. The interior portion 8B is disposed inside the locking portion 5B and includes the inner tubular member 9B whose configuration is different from the interior portion 8 described in the first embodiment.

As illustrated in FIG. 11, the outer tubular member 4B of the exterior portion 3B is a tubular member in which a plurality of through-holes 35 are formed on an outer circumferential surface. The plurality of through-holes 35 formed on an outer circumferential surface of the outer tubular member 4B are arranged in a row or randomly at positions separated from each other in a circumferential direction of the outer tubular member 4B. The plurality of through-holes 35 formed on the outer circumferential surface of the outer tubular member 4B are arranged at positions separated from each other in a center line direction of the outer tubular member 4B.

As illustrated in FIG. 12, the locking portion 5B includes the intermediate tubular member 36 and a plurality of anchors 37. The intermediate tubular member 36 is a tubular member disposed between the outer tubular member 4B and the inner tubular member 9B. The plurality of anchors 37 are fixed to an external surface of the intermediate tubular member 36.

A distal end of the intermediate tubular member 36 is positioned at a position of a distal end of the outer tubular member 4B or more proximal than the position of the distal end of the outer tubular member 4B. A proximal end of the intermediate tubular member 36 is positioned more proximal than a proximal end of the outer tubular member 4B. A proximal part of the intermediate tubular member 36 is a first grasping portion 36a that the operator holds to rotate the intermediate tubular member 36 with his or her hand. The inner tubular member 9B is inserted into the intermediate tubular member 36.

A center line of the intermediate tubular member 36 is aligned to be substantially coaxial with both a center line of the outer tubular member 4B and a center line of the inner tubular member 9B. The intermediate tubular member 36 is rotatable with respect to the outer tubular member 4B and the inner tubular member 9B.

The anchor 37 includes a wire 38 and an end member 39. The wire 38 is fixed to an outer circumferential surface of the intermediate tubular member 36. The end member 39 is fixed to an end of the wire 38.

The wire 38 of the anchor 37 has a restoring force that restores it to a substantially linear shape when no external force is applied. The wire 38 of the anchor 37 includes one end that is inserted into, for example, a sidewall of the intermediate tubular member 36 and is fixed to the intermediate tubular member 36 by, for example, bonding. In the present embodiment, each of the wires 38 of the anchor 37 is fixed perpendicularly to the outer circumferential surface of the intermediate tubular member 36.

The end member 39 of the anchor 37 has a curved surface so as not to stimulate mucous membranes. In the present embodiment, the end member 39 of the anchor 37 is a spherical member into which an end of the wire 38 of the anchor 37 is inserted and fixed. An outer diameter of the end member 39 is greater than an inner diameter of the through-hole 35 formed on the outer circumferential surface of the outer tubular member 4B.

As illustrated in FIG. 13, the interior portion 8B includes the inner tubular member 9B and the contact portion 11B. The inner tubular member 9B has a substantially tubular shape whose side is open at a distal portion and whose proximal end is open. The contact portion 11B is provided at a distal end of the inner tubular member 9B. In addition, a proximal part of the inner tubular member 9B in the interior portion 8B is a second grasping portion 9a that the operator can grasp to rotate the inner tubular member 9B about the center line of the inner tubular member 9B.

A side opening at a distal portion of the inner tubular member 9B is an opening through which a conductive member 17B to be described below protrudes. That is, in the present embodiment, the conductive member 17B is inserted into a distal side from a proximal end of the inner tubular member 9B, and the conductive member 17B protrudes from the side opening at the distal portion of the inner tubular member 9B.

As illustrated in FIG. 15, the side opening at the distal portion of the inner tubular member 9B has a curved surface or a flat surface inclined with respect to the center line of the inner tubular member 9B inside the inner tubular member 9B. Accordingly, the conductive member 17B inserted from the proximal side to the distal side along the center line of the inner tubular member 9B protrudes in a direction inclined with respect to the center line of the inner tubular member 9B in the opening. In the present embodiment, similarly to the guide hole 14 described in the first embodiment, the side opening at the distal portion of the inner tubular member 9B is a guide hole 14B for guiding the distal end of the conductive member 17B toward a boundary part between the uterine cervix and the vaginal canal.

The contact portion 11B has a disc shape along a plane perpendicular to the center line of the inner tubular member 9. Similarly to the first embodiment, the contact portion 11B of the present embodiment may have a cup shape having a concave portion that is contactable on the uterine cervix. The vaginal portion of the cervix is contactable on an external surface of a distal side of the contact portion 11B. Similarly to the concave portion 13 described in the first embodiment, a position of the conductive member 17B can be determined such that the conductive member 17B is directed toward the boundary part between the uterine cervix and the vaginal canal.

As illustrated in FIG. 14, as the incision portion 16B, for example, a known high-frequency incision instrument having a needle-type electrode can be appropriately selected and used. As an example, the incision portion 16B includes an insulating member 18B (for example, an insulating sheath), the conductive member 17B (for example, a needle-type electrode) and an operating portion 20B. The insulating member 18B corresponds to the insulating member 18 described in the first embodiment. The conductive member 17B (for example, a needle-type electrode) corresponds to the conductive member 17 described in the first embodiment and is inserted into the insulating member 18B. The operating portion 20B is fixed to the proximal end of the insulating member 18B. The operating portion 20B is provided to advance and retract the conductive member 17B.

Figure 18:
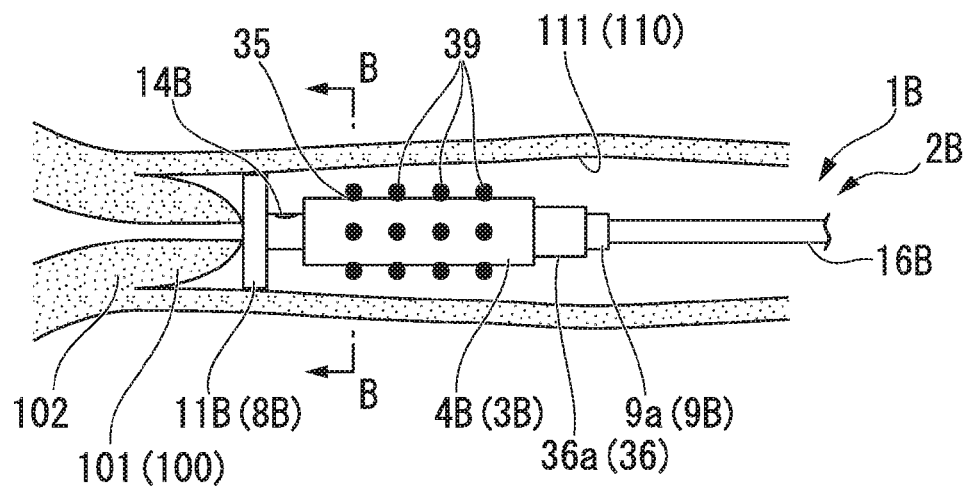
FIG. 18 is a diagram describing a procedure using the vaginal wall incision instrument according to the third embodiment of the present invention.
Figure 19:
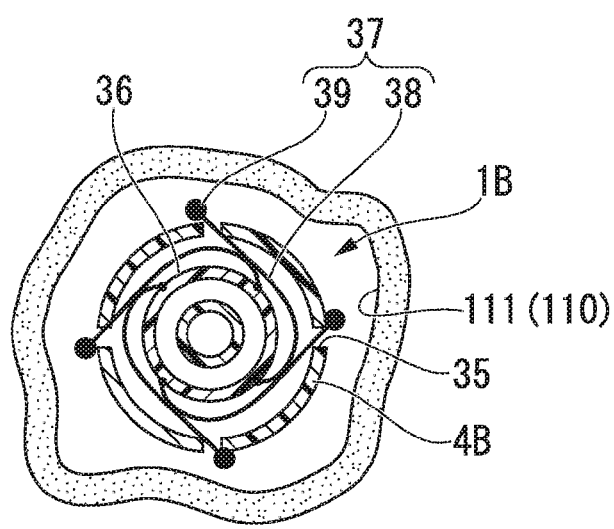
FIG. 19 is a diagram describing a procedure using the vaginal wall incision instrument according to the third embodiment of the present invention and is a cross-sectional view taken along line B-B of FIG. 18.
Figure 20:
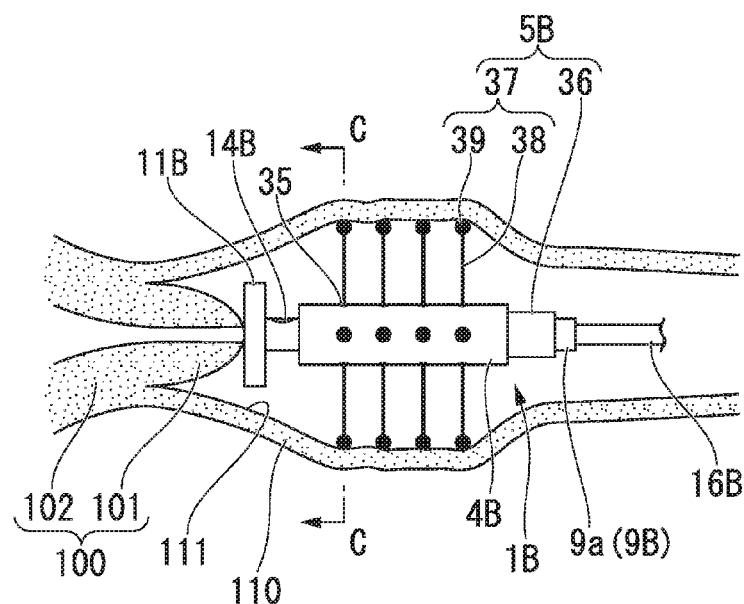
FIG. 20 is a diagram describing a procedure using the vaginal wall incision instrument according to the third embodiment of the present invention.
Figure 21:
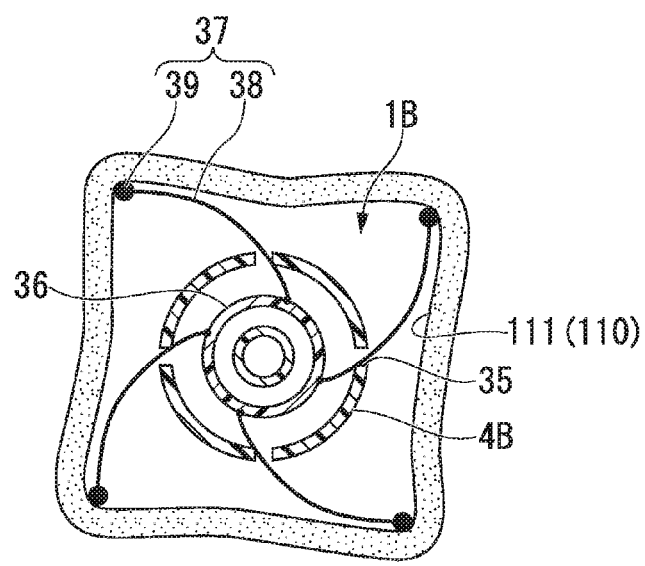
FIG. 21 is a diagram describing a procedure using the vaginal wall incision instrument according to the third embodiment of the present invention and is a cross-sectional view taken along line C-C of FIG. 20.
Figure 22:
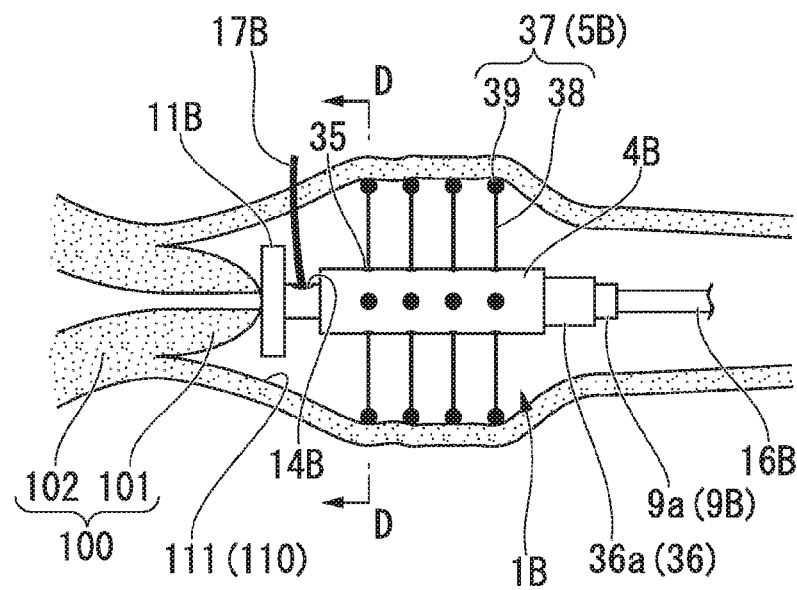
FIG. 22 is a diagram describing a procedure using the vaginal wall incision instrument according to the third embodiment of the present invention.
Figure 23:
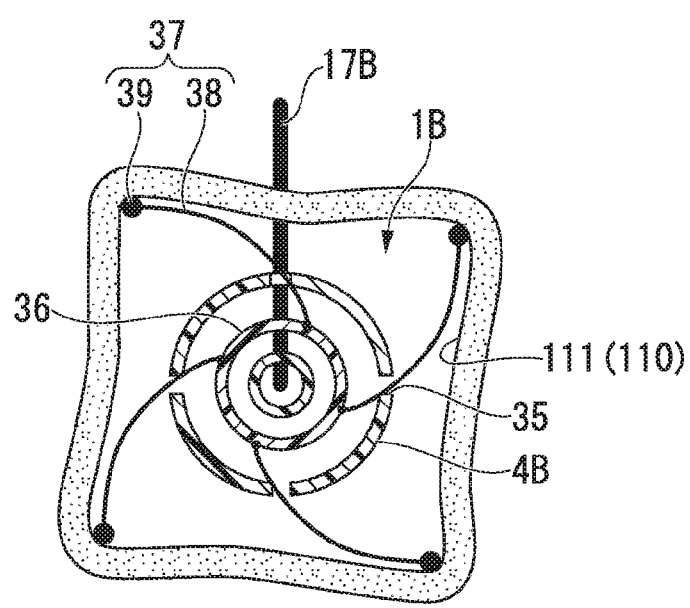
FIG. 23 is a diagram describing a procedure using the vaginal wall incision instrument according to the third embodiment of the present invention and is a cross-sectional view taken along line D-D of FIG. 22.
Figure 24:
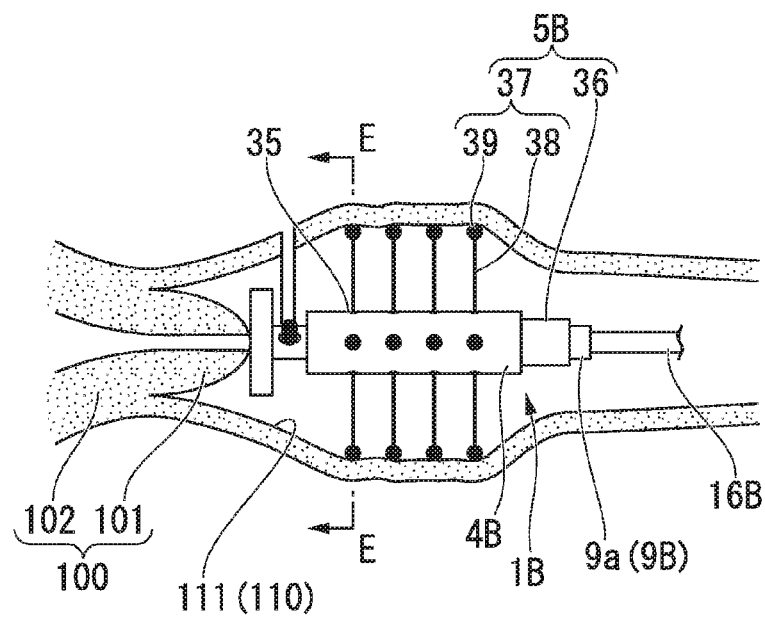
FIG. 24 is a diagram describing a procedure using the vaginal wall incision instrument according to the third embodiment of the present invention.
Figure 25:
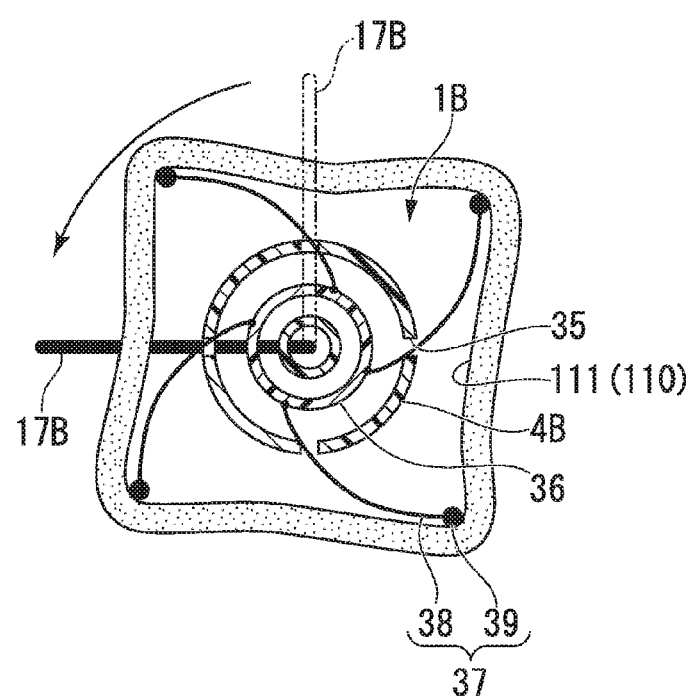
FIG. 25 is a diagram describing a procedure using the vaginal wall incision instrument according to the third embodiment of the present invention and is a cross-sectional view taken along line E-E of FIG. 24.

Next, an operation of the vaginal wall incision instrument 1B according to the present embodiment will be described. FIG. 18 is a diagram describing a procedure using the vaginal wall incision instrument 1B according to the present embodiment. FIG. 19 is a diagram describing a procedure using the vaginal wall incision instrument 1B according to the present embodiment and is a cross-sectional view taken along line B-B of FIG. 18. FIG. 20 is a diagram describing a procedure using the vaginal wall incision instrument 1B according to the present embodiment. FIG. 21 is a diagram describing a procedure using the vaginal wall incision instrument 1B according to the present embodiment and is a cross-sectional view taken along line C-C of FIG. 20. FIG. 22 is a diagram describing a procedure using the vaginal wall incision instrument 1B according to the present embodiment. FIG. 23 is a diagram describing a procedure using the vaginal wall incision instrument 1B according to the present embodiment and is a cross-sectional view taken along line D-D of FIG. 22. FIG. 24 is a diagram describing a procedure using the vaginal wall incision instrument 1B according to the present embodiment. FIG. 25 is a diagram describing a procedure using the vaginal wall incision instrument 1B according to the present embodiment and is a cross-sectional view taken along line E-E of FIG. 24.

In the present embodiment, when the operator rotates the intermediate tubular member 36 using the center line of the intermediate tubular member 36 as a center line of rotation with respect to the outer tubular member 4B, the wire 38 of the anchor 37 can be inserted into or extracted from the through-hole 35 of the outer tubular member 4B.

That is, as illustrated in FIGS. 18 and 19, when the operator inserts the main body portion 2B into the vaginal canal 110, the wire 38 of the anchor 37 is wound on the outer circumferential surface of the intermediate tubular member 36 (refer to FIG. 16). Next, while the main body portion 2B is completely inserted into the vaginal canal 110 and the contact portion 11B is in contact with the first part 101, the operator rotates the intermediate tubular member 36 with respect to the outer tubular member 4B and unwinds the wire 38 of the anchor 37 on the intermediate tubular member 36. As a result, the wire 38 of the anchor 37 is pushed to the outside of the outer tubular member 4B through each of the through-holes 35 on the outer circumferential surface of the outer tubular member 4B while returning to a linear state (refer to FIG. 17). The restoring force that restores the wire 38 to the linear state is exerted on the wire 38 of the anchor 37. Accordingly, the wire 38 may be pushed to the outside of the outer tubular member 4B through each of the through-holes 35 of the outer tubular member 4B only when a force with which the wire 38 is wound on the intermediate tubular member 36 is released according to a magnitude of the restoring force of the wire 38.

As a result, as illustrated in FIGS. 20 and 21, the wire 38 of the anchor 37 presses the vaginal wall 111 in a radially outward direction thereof through the end member 39. According to a frictional force between each of the end members 39 fixed to the wire 38 of the anchor 37 and the vaginal wall 111, the outer tubular member 4B is locked to the vaginal wall 111, similarly to the locking portion 5 described in the first embodiment. When each of the wires 38 has the restoring force that pushes the wire 38 to the outside of the outer tubular member 4B through each of the through-holes 35 of the outer tubular member 4B only by releasing a force with which the wire 38 is wound on the intermediate tubular member 36, rotation of the intermediate tubular member 36 stops at a position at which magnitudes of the restoring force of each of the wires 38 and a counterforce from the vaginal wall 111 become equal.

After the outer tubular member 4B is locked to the vaginal wall 111 by the anchor 37, as illustrated in FIGS. 22 and 23, the operator protrudes the conductive member 17B from the guide hole 14B, which is the side opening at the distal portion of the inner tubular member 9. As a result, similarly to the first embodiment, the distal end of the conductive member 17B penetrates through the vaginal wall 111, and is in a state in which the conductive member 17B penetrates through the vaginal wall 111 in the boundary part between the uterine cervix 102 and the vaginal canal 110.

Next, while a high-frequency current is supplied to the conductive member 17B, the operator rotates the second grasping portion 9a using the center line of the inner tubular member 9B as a center line of rotation, as illustrated in FIGS. 24 and 25. As a result, with respect to the vaginal wall 111 locked to the outer tubular member 4B by the locking portion 5B, the conductive member 17B is rotated using the center line of the vaginal canal 110 as a center line of rotation. Accordingly, similarly to the first embodiment, the conductive member 17B separates the vaginal wall 111 over the entire circumference.

Similarly to the first embodiment, in the present embodiment, it is also possible to easily separate the vaginal wall 111 along an ideal separating line in the boundary between the uterine cervix 102 and the vaginal canal 110.

In the present embodiment, an operation of appropriately adjusting a length of the wire 38 of the anchor 37 can be easily performed by adjusting an amount of rotation of the intermediate tubular member 36 with respect to the outer tubular member 4B.

When each of the wires 38 has the restoring force that pushes the wire 38 to the outside of the outer tubular member 4B through each of the through-holes 35 of the outer tubular member 4B only by releasing a force with which the wire 38 is wound on the intermediate tubular member 36, rotation of the intermediate tubular member 36 stops at the position at which magnitudes of the restoring force of each of the wires 38 and the counterforce from the vaginal wall 111 become equal. Therefore, regardless of individual differences of patients, it is possible to lock the outer tubular member 4B to the vaginal wall 111 with a constant locking force.

(Fourth Embodiment)

Figure 26:
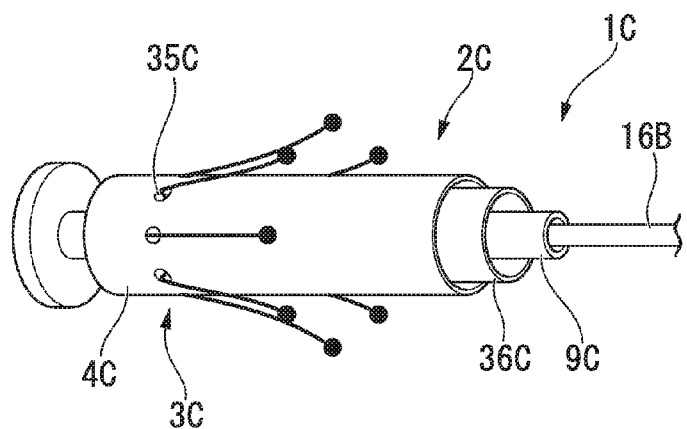
FIG. 26 is a general view of a vaginal wall incision instrument according to a fourth embodiment of the present invention.
Figure 27:
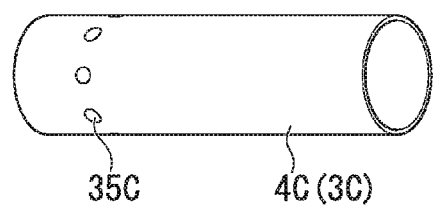
FIG. 27 is a perspective view of an outer tubular member of the vaginal wall incision instrument according to the fourth embodiment of the present invention.
Figure 28:
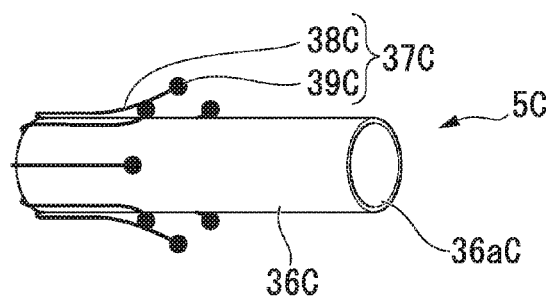
FIG. 28 is a perspective view of an intermediate tubular member of the vaginal wall incision instrument according to the fourth embodiment of the present invention.
Figure 29:
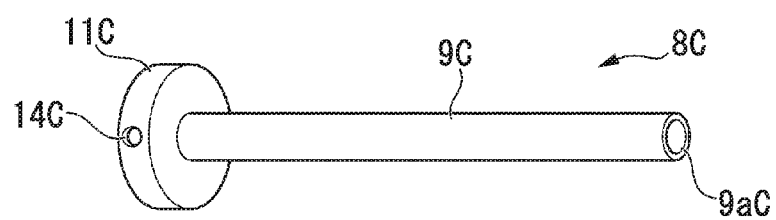
FIG. 29 is a perspective view of an inner tubular member of the vaginal wall incision instrument according to the fourth embodiment of the present invention.
Figure 30:
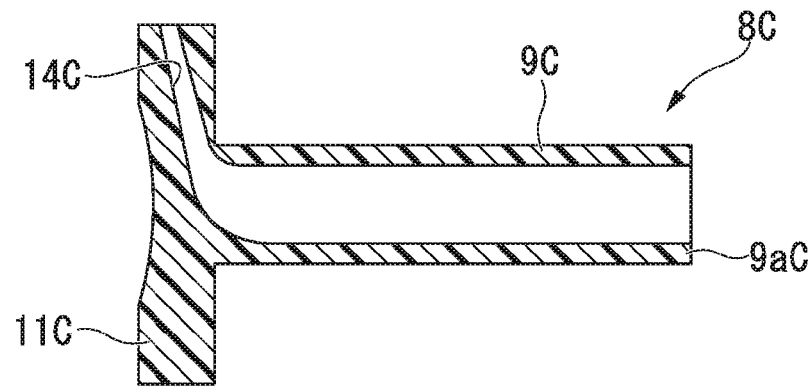
FIG. 30 is a cross-sectional view of the inner tubular member of the vaginal wall incision instrument according to the fourth embodiment of the present invention.

Next, a fourth embodiment of the present invention will be described. FIG. 26 is a general view of a vaginal wall incision instrument 1C according to the present embodiment. FIG. 27 is a perspective view of an outer tubular member 4C of the vaginal wall incision instrument 1C according to the present embodiment. FIG. 28 is a perspective view of an intermediate tubular member 36C of the vaginal wall incision instrument 1C according to the present embodiment. FIG. 29 is a perspective view of an inner tubular member 9C of the vaginal wall incision instrument 1C according to the present embodiment. FIG. 30 is a cross-sectional view of the inner tubular member 9C of the vaginal wall incision instrument 1C according to the present embodiment.

As illustrated in FIG. 26, the vaginal wall incision instrument 1C according to the present embodiment includes a main body portion 2C whose configuration is different from the main body portion 2 described in the first embodiment. The vaginal wall incision instrument 1C according to the present embodiment includes the incision portion 16B described in the third embodiment instead of the incision portion 16 described in the first embodiment.

The main body portion 2C includes an exterior portion 3C, a locking portion 5C, and an interior portion 8C. The exterior portion 3C includes the outer tubular member 4C whose shape is different from the outer tubular member 4 described in the first embodiment. The locking portion 5C is disposed inside the exterior portion 3C and has a different configuration from the locking portion 5 described in the first embodiment. The interior portion 8C is disposed inside the locking portion 5C and includes the inner tubular member 9C whose configuration is different from the interior portion 8 described in the first embodiment.

As illustrated in FIG. 27, the outer tubular member 4C of the exterior portion 3C is a tubular member in which a plurality of through-holes 35C are formed on an outer circumferential surface. The plurality of through-holes 35C of the outer tubular member 4C are arranged in a row or randomly at positions separated from each other in a circumferential direction of the outer tubular member 4C.

As illustrated in FIG. 28, the locking portion 5C includes the intermediate tubular member 36C and a plurality of anchors 37C. The intermediate tubular member 36C is a tubular member disposed between the outer tubular member 4C and the inner tubular member 9C. The plurality of anchors 37C are fixed to an external surface of the intermediate tubular member 36C.

A distal end of the intermediate tubular member 36C is positioned at a position of a distal end of the outer tubular member 4C or more proximal than the distal end of the outer tubular member 4C. A proximal end of the intermediate tubular member 36C is positioned more proximal than a proximal end of the outer tubular member 4C. A proximal part of the intermediate tubular member 36C is a first grasping portion 36aC that the operator holds to advance and retract the intermediate tubular member 36C with respect to the outer tubular member 4C with his or her hand. The inner tubular member 9C is inserted into the intermediate tubular member 36C.

A center line of the intermediate tubular member 36C 36 is aligned to be substantially coaxial with both a center line of the outer tubular member 4C and a center line of the inner tubular member 9C. The intermediate tubular member 36C can advance and retract in a center line direction of the outer tubular member 4C with respect to the outer tubular member 4C. The intermediate tubular member 36C is rotatable using the center line of the inner tubular member 9C as a center line of rotation with respect to the inner tubular member 9C.

The anchor 37C includes a wire 38C and an end member 39C. The wire 38C is fixed to an outer circumferential surface of the intermediate tubular member 36C. The end member 39C is fixed to an end of the wire 38C.

The wire 38C of the anchor 37C has a restoring force with which the wire can be restored to a substantially linear shape when no external force is applied. One end of the wire 38C of the anchor 37C is fixed to the intermediate tubular member 36C by, for example, bonding, to be inserted into, for example, a sidewall of the intermediate tubular member 36C, or along the outer circumferential surface of the intermediate tubular member 36C. The wire 38C of the anchor 37C is fixed to be inclined such that it is gradually separated from the outer circumferential surface of the intermediate tubular member 36C from the distal end of the intermediate tubular member 36C to a proximal side on an outer circumferential surface of the distal end of the intermediate tubular member 36C.

The end member 39C of the anchor 37C has a curved surface so as not to stimulate mucous membranes. In the present embodiment, the end member 39C of the anchor 37C is the same spherical member as in the third embodiment. An outer diameter of the end member 39C is greater than an inner diameter of the through-hole 35C formed on an outer circumferential surface of the outer tubular member 4C.

As illustrated in FIG. 29, the interior portion 8C includes the inner tubular member 9C having a cylindrical shape and the contact portion 11C. The contact portion 11C communicates with an inside of the inner tubular member 9C provided at a distal end of the inner tubular member 9C. In addition, a proximal part of the inner tubular member 9C in the interior portion 8C is a second grasping portion 9aC that the operator can grasp to rotate the inner tubular member 9C about the center line of the inner tubular member 9B.

As illustrated in FIG. 30, a guide hole 14C is formed in the contact portion 11C. The guide hole 14C is formed to protrude the conductive member 17B inserted into a distal side from a proximal side of the inner tubular member 9C in a radially outward direction of the inner tubular member 9C.

Similarly to the guide hole 14 of the first embodiment, the guide hole 14C supports the conductive member 17B such that the distal end of the conductive member 17B can penetrate through the boundary part between the uterine cervix and the vaginal canal. In the present embodiment, the insulating member 18B of the incision portion 16B is not fixed to an inner surface of the guide hole 14C.

Similarly to the third embodiment, the contact portion 11C has a disc shape along a plane perpendicular to the center line of the inner tubular member 9. The first part 101 is contactable on an external surface of a distal side in the contact portion 11B. Similarly to the concave portion 13 described in the first embodiment, a position of the conductive member 17B can be determined such that the conductive member 17B is directed toward the boundary part between the uterine cervix and the vaginal canal.

Figure 31:
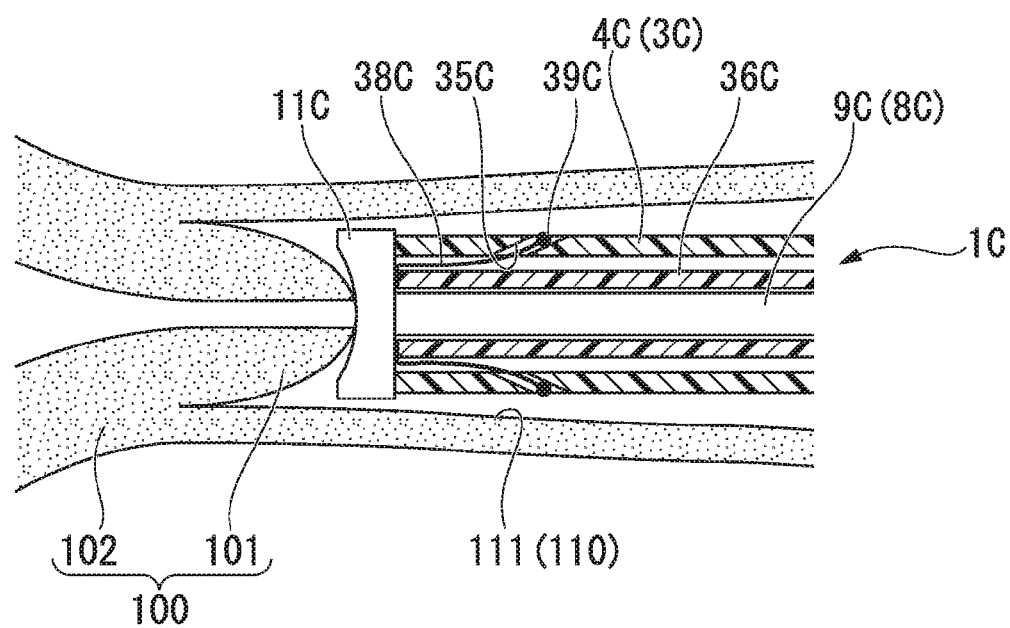
FIG. 31 is a diagram describing an operation of the vaginal wall incision instrument according to the fourth embodiment of the present invention.
Figure 32:
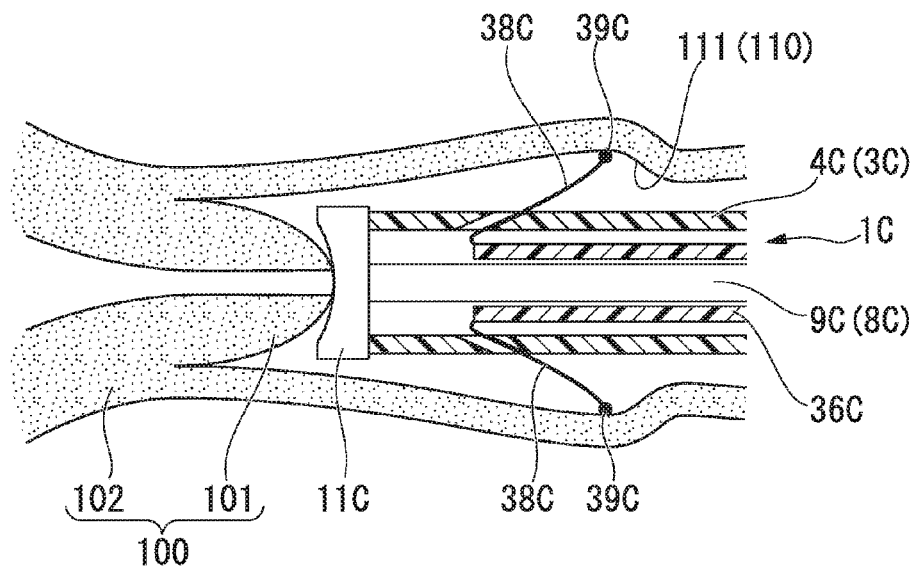
FIG. 32 is a diagram describing an operation of the vaginal wall incision instrument according to the fourth embodiment of the present invention.

Next, an operation of the vaginal wall incision instrument 1C according to the present embodiment will be described. FIG. 31 is a diagram describing an operation of the vaginal wall incision instrument 1C according to the present embodiment. FIG. 32 is a diagram describing an operation of the vaginal wall incision instrument 1C according to the present embodiment. FIGS. 33 to 36 are diagrams describing a procedure using the vaginal wall incision instrument 1C according to the present embodiment.

As illustrated in FIGS. 31 and 32, in the present embodiment, when the operator advances and retracts the intermediate tubular member 36C with respect to the outer tubular member 4C along the center line of the intermediate tubular member 36C, the wire 38C of the anchor 37C can be inserted into or extracted from the through-hole 35C of the outer tubular member 4C.

Figure 33:
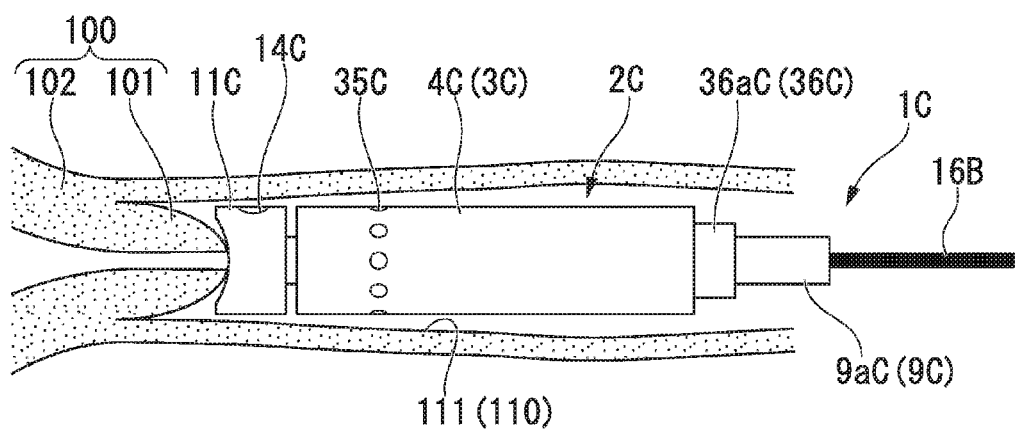
FIG. 33 is a diagram describing a procedure using the vaginal wall incision instrument according to the fourth embodiment of the present invention.
Figure 34:
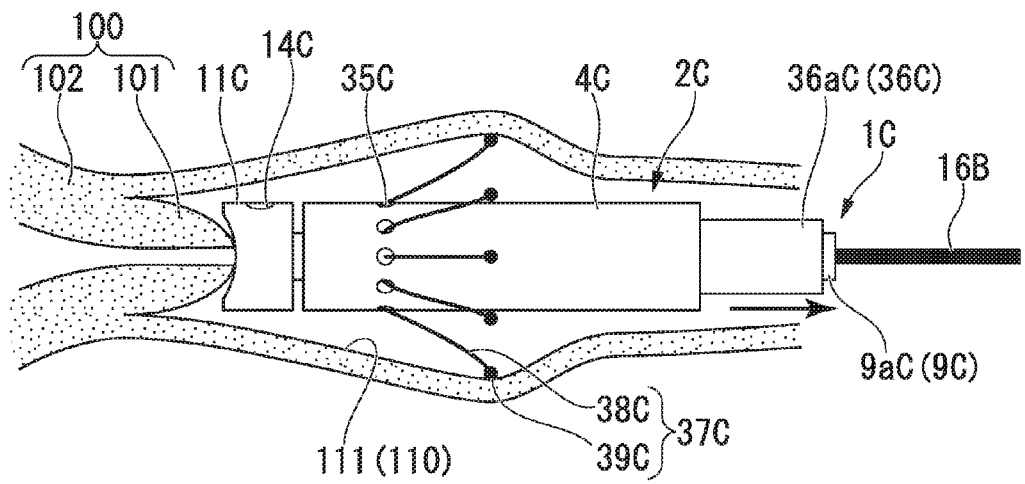
FIG. 34 is a diagram describing a procedure using the vaginal wall incision instrument according to the fourth embodiment of the present invention.
Figure 35:
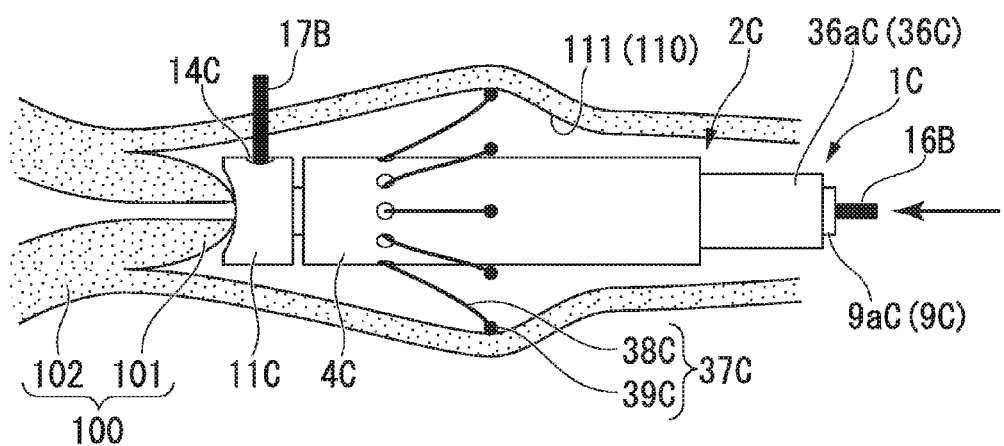
FIG. 35 is a diagram describing a procedure using the vaginal wall incision instrument according to the fourth embodiment of the present invention.

That is, as illustrated in FIG. 33, when the main body portion 2C is inserted into the vaginal canal 110, the intermediate tubular member 36C is pressed against a distal side of the outer tubular member 4C such that the wire 38C of the anchor 37C is accommodated in a gap between the intermediate tubular member 36C and the outer tubular member 4C. Then, while the main body portion 2C is completely inserted into the vaginal canal 110 and the contact portion 11C is in contact with the first part 101, the operator moves the intermediate tubular member 36C to a proximal side of the outer tubular member 4C as illustrated in FIG. 34. As a result, the wire 38C of the anchor 37C is pushed to the outside of the outer tubular member 4C through the through-hole 35C on the outer circumferential surface of the outer tubular member 4C. The wire 38C of the anchor 37C is distorted in a radially outward direction of the outer tubular member 4C by an inner surface of the through-hole 35C of the outer tubular member 4C. Therefore, at the outside of the outer tubular member 4C, while the wire 38C of the anchor 37C is inclined to be gradually separated from the outer circumferential surface of the outer tubular member 4C as it advances to the proximal side of the outer tubular member 4C, the end member 39C presses the vaginal wall 111.

As a result, the wire 38C of the anchor 37C presses the vaginal wall 111 in a radially outward direction of the vaginal wall 111 through the end member 39C. According to a frictional force between each of the end members 39C fixed to the wire 38C of the anchor 37C and the vaginal wall 111, the outer tubular member 4C is locked to the vaginal wall 111, similarly to the locking portion 5 described in the first embodiment.

The outer tubular member 4C is locked to the vaginal wall 111 by the locking portion 5C having the anchor 37C, and then the operator protrudes the conductive member 17B from the guide hole 14C. As a result, similarly to the first embodiment, the distal end of the conductive member 17B penetrates through the vaginal wall 111, and the conductive member 17B penetrates through the vaginal wall 111 in the boundary part between the uterine cervix 102 and the vaginal canal 110 (refer to FIG. 35).

Figure 36:
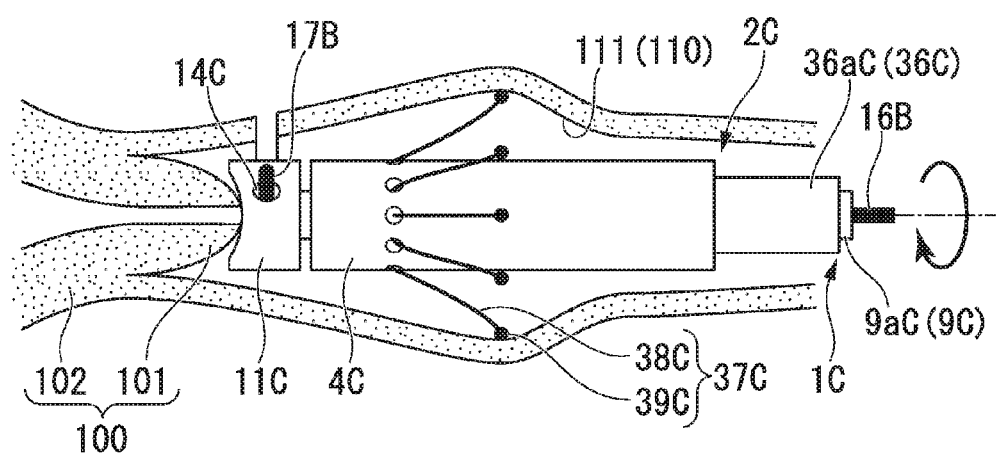
FIG. 36 is a diagram describing a procedure using the vaginal wall incision instrument according to the fourth embodiment of the present invention.

Next, while a high-frequency current is supplied to the conductive member 17B, the operator rotates the second grasping portion 9aC using the center line of the inner tubular member 9C as a center line of rotation, as illustrated in FIG. 36. As a result, with respect to the vaginal wall 111 locked to the outer tubular member 4C by the locking portion 5C, the conductive member 17B is rotated using the center line of the vaginal canal 110 as a center line of rotation. Accordingly, similarly to the first embodiment, the conductive member 17B separates the vaginal wall 111 over the entire circumference.

Similarly to the first embodiment, the vaginal wall incision instrument 1C according to the present embodiment can also easily separate the vaginal wall 111 along an ideal separating line in the boundary between the uterine cervix 102 and the vaginal canal 110.

In the present embodiment, an operation of appropriately adjusting a length of the wire 38 of the anchor 37 can be easily performed by adjusting an amount of a forward movement or an amount of a backward movement of the intermediate tubular member 36 with respect to the outer tubular member 4C.

While the embodiments of the present invention have been described above with reference to the accompanying drawings, a detailed configuration is not limited to the embodiments and design modifications without departing from the scope of the present invention are also included.

For example, in the above-described embodiments, an exemplary conductor through which a high-frequency current is supplied was disclosed as the incision portions 16 and 16B. However, in the vaginal wall incision instrument of the present invention, an incision portion that incises biological tissues using an ultrasound or laser may be provided instead of the incision portion made of a conductor.

(Note)

According to another aspect of the present invention, a method of separating a vaginal wall is provided. In a boundary between the vaginal canal and the uterine cervix, an incision portion (knife) penetrates from an inside of the vaginal canal into the abdominal cavity. While the knife has penetrated through the vaginal canal, the knife is rotated using a center line of the vaginal canal as a center line of rotation, and thereby the vaginal canal is separated over the entire circumference.

According to the method, the uterus and the vaginal canal can be separated using the boundary part between the uterine cervix and the vaginal canal as a separating line.

In addition, in the method, the knife may penetrate through the vaginal canal in a direction intersecting a center line of the vaginal canal and at an angle away from the uterine cervix and the uterine corpus.

In addition, in the method, a contact portion that is contactable on the vaginal portion of the cervix may be inserted into the vaginal canal and the knife may be supported by the contact portion.

In addition, a position-determining member that can be inserted into the orifice of the uterus may be inserted into the orifice of the uterus, and the position-determining member may regulate a movement direction of the knife to a rotation direction in which the orifice of the uterus is used as a center line of rotation.

While preferred embodiments of the invention have been described and illustrated above, it should be understood that these are exemplary of the invention and are not to be considered as limiting. Additions, omissions, substitutions, and other modifications can be made without departing from the spirit and scope of the present invention. Accordingly, the invention is not to be considered as being limited by the foregoing description, and is only limited by the scope of the appended claims.

What is claimed is:

1. A vaginal wall incision instrument, comprising:
an exterior portion that includes an outer tubular member having an outer surface;
an interior portion that includes:
an inner tubular member disposed inside the outer tubular member, and
a cup-shaped member that is fixed to a distal end of the inner tubular member, the interior portion being rotatable with respect to the outer tubular member;
a guide hole that extends in a direction inclined with respect to a center axis of the inner tubular member and that pierces through a surface of the cup-shaped member;
an insulating member that has a tubular shape and a distal end fixed to an inner surface of the guide hole, at least part of the insulating member being disposed inside the inner tubular member;
a conductive member that has electrical conductivity and is inserted inside the insulating member such that the conductive member is configured to advance from and retract into the insulating member; and
an operating portion that is disposed at a proximal part of the inner tubular member, the operating portion being configured to adjust an amount of protrusion of the conductive member from the insulating member,
wherein the guide hole is configured to guide the conductive member toward a boundary between the uterine cervix and the vaginal canal when the cup-shaped member is in contact with the uterine cervix.

2. The vaginal wall incision instrument according to claim 1, wherein the exterior portion further comprises an airtight valve configured to hermetically seal a gap between the outer tubular member and the interior portion.

3. The vaginal wall incision instrument according to claim 1, wherein the exterior portion includes a locking portion that protrudes from an outer circumferential surface of the exterior portion in a radially outward direction of the exterior portion and is lockable to the inner wall of the vaginal canal.

4. The vaginal wall incision instrument according to claim 3, wherein the locking portion includes a plurality of anchors that are lockable to the inner wall of the vaginal canal.

5. The vaginal wall incision instrument according to claim 2, wherein the operating portion includes:
a shaft body having a substantially bar shape;
a serrated portion provided on an external surface of the shaft body;
a slider attached to the shaft body; and
a convex portion that is provided in the slider and engageable with a plurality of projections constituting the serrated portion.

6. The vaginal wall incision instrument according to claim 2, wherein the cup-shaped member is formed such that a diameter of the cup-shaped member gradually increases toward a distal side and has an inner surface that is contactable on the uterine cervix.

7. The vaginal wall incision instrument according to claim 2, wherein the interior portion includes a bar-shaped position-determining member that is formed to be coaxial with the center line of rotation of the interior portion and protrudes toward a distal side.

* * * * *